United States Patent
Yang et al.

(10) Patent No.: US 11,104,633 B2
(45) Date of Patent: Aug. 31, 2021

(54) CANCER TREATMENT USING COMPOUNDS THAT SELECTIVELY TARGET POLYPLOID CANCER CELLS FOR DISRUPTION

(71) Applicant: Chengdu Anticancer Bioscience, Ltd., Chengdu (CN)

(72) Inventors: Dun Yang, South San Francisco, CA (US); Jing Zhang, Fife (GB); Shenqiu Zhang, Fife (GB)

(73) Assignee: Chengdu Anticancer Bioscience, Ltd., Chengdu (CN)

(*) Notice: Subject to any disclaimer, the term of this patent is extended or adjusted under 35 U.S.C. 154(b) by 0 days.

(21) Appl. No.: 15/985,115

(22) Filed: May 21, 2018

(65) Prior Publication Data

US 2020/0140364 A1    May 7, 2020

Related U.S. Application Data

(60) Provisional application No. 62/513,958, filed on Jun. 1, 2017.

(51) Int. Cl.
| | | |
|---|---|---|
| *C07C 50/28* | (2006.01) | |
| *A61P 35/00* | (2006.01) | |
| *A61K 45/06* | (2006.01) | |

(52) U.S. Cl.
CPC .............. *C07C 50/28* (2013.01); *A61P 35/00* (2018.01); *A61K 45/06* (2013.01)

(58) Field of Classification Search
None
See application file for complete search history.

(56) References Cited

PUBLICATIONS

Choudhary et al., Identification of Selective Lead Compounds for Treatment of High-Ploidy Breast Cancer, Mol Cancer Ther, 15 (2016) 48-59.
Jemaa et al., Preferential Killing of Tetraploid Colon Cancer Cells by Targeting the Mitotic Kinase PLK1, Cell Physiol Biochem, 54 (2020) 303-320.
Kawakami et al., New Cell Cycle Inhibitors Target Aneuploidy in Cancer Therapy, Annu Rev Pharmacol Toxicol, 59 (2019) 361-377.
McKenzie et al., Investigating cytokinesis failure as a strategy in cancer therapy, Oncotarget, 7 (2016) 87323-87341.
Mittal et al., Multinucleated polyploidy drives resistance to Docetaxel chemotherapy in prostate cancer, Br J Cancer, 116 (2017) 1186-1194.
Prabhu et al., Embelin: a benzoquinone possesses therapeutic potential for the treatment of human cancer, Future Med Chem, 10 (2018) 961-976.
Sadaie et al., Cell-based screen for altered nuclear phenotypes reveals senescence progression in polyploid cells after Aurora kinase B inhibition, Mol Biol Cell, 26 (2015) 2971-2985.
Singh et al., Synthesis and anti-proliferative activities of new derivatives of embelin, Bioorg Med Chem Lett, 24 (2014) 4865-4870.
Vittoria et al., A genome-wide microRNA screen identifies regulators of tetraploid cell proliferation, Mol Biol Cell, 29 (2018) 1682-1692.
Wrobel-Biedrawa et al., Anti-melanoma potential of two benzoquinone homologues embelin and rapanone—a comparative in vitro study, Toxicol In Vitro, 65 (2020) 104826.
Yang et al., Therapeutic potential of a synthetic lethal interaction between the MYC proto-oncogene and inhibition of aurora-B kinase, Proc Natl Acad Sci U S A, 107 (2010) 13836-13841.
Zhang et al., The anti-apoptotic proteins Bcl-2 and Bcl-xL suppress Beclin1/Atg6-mediated lethal autophagy in polyploid cells, Exp Cell Res, (2020) 112112.
Zhang et al., CyclinG1 Amplification Enhances Aurora Kinase Inhibitor-Induced Polyploid Resistance and Inhibition of Bcl-2 Pathway Reverses the Resistance, Cell Physiol Biochem, 43 (2017) 94-107.
Zhou et al., Inhibition of Bcl-xL overcomes polyploidy resistance and leads to apoptotic cell death in acute myeloid leukemia cells, Oncotarget, 6 (2015) 21557-21571.

*Primary Examiner* — Ana Z Muresan
(74) *Attorney, Agent, or Firm* — Goodwin Procter LLP

(57) ABSTRACT

The disclosure provides a compound of Formula I:

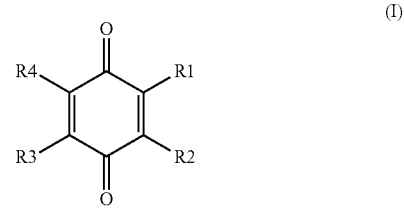

(I)

or a pharmaceutically acceptable salt thereof, wherein $R^1$, $R^2$, $R^3$, and $R^4$ are as described herein. The disclosure also provides methods for identifying a compound that selectively kills polyploid cells, and methods for killing polyploid tumor cells by administering a compound of Formula I to a patient in need thereof.

19 Claims, 11 Drawing Sheets

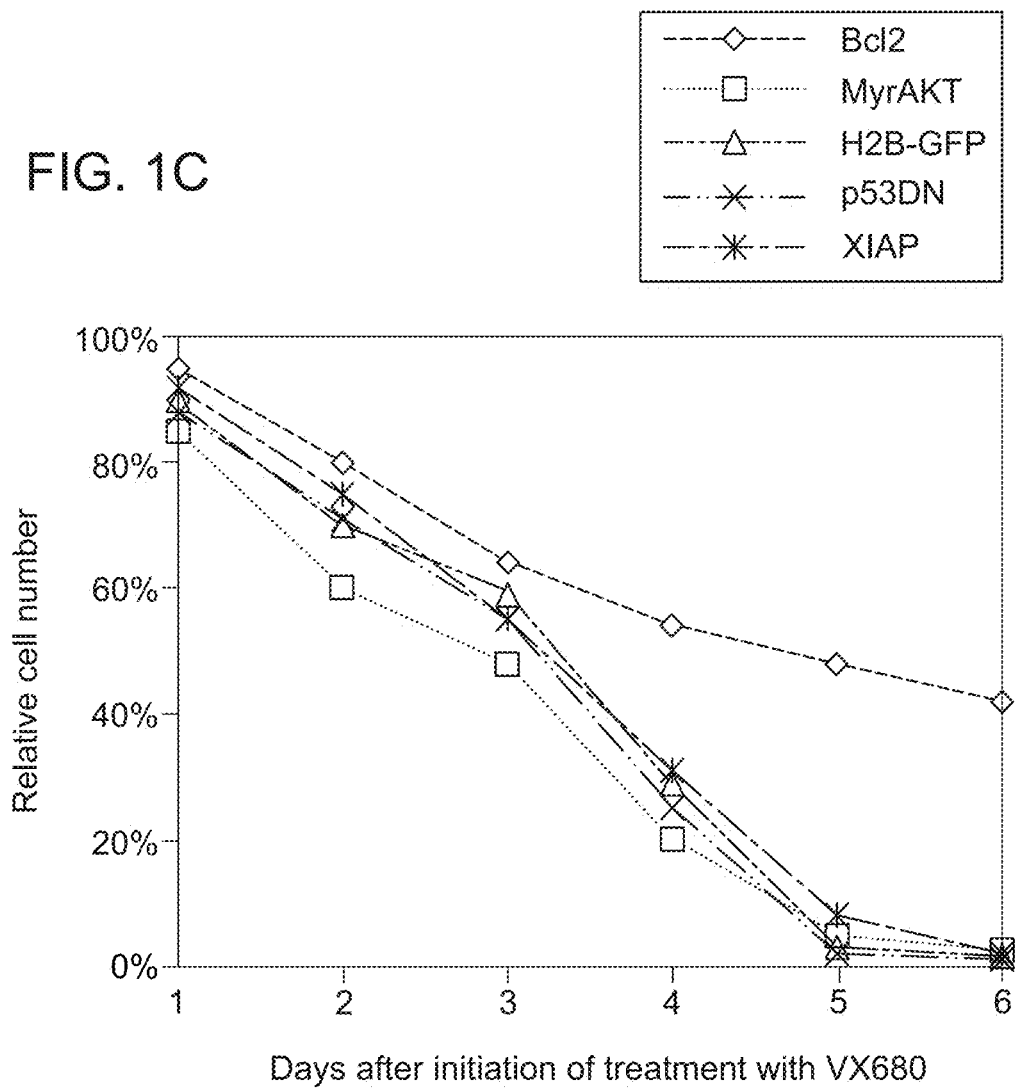

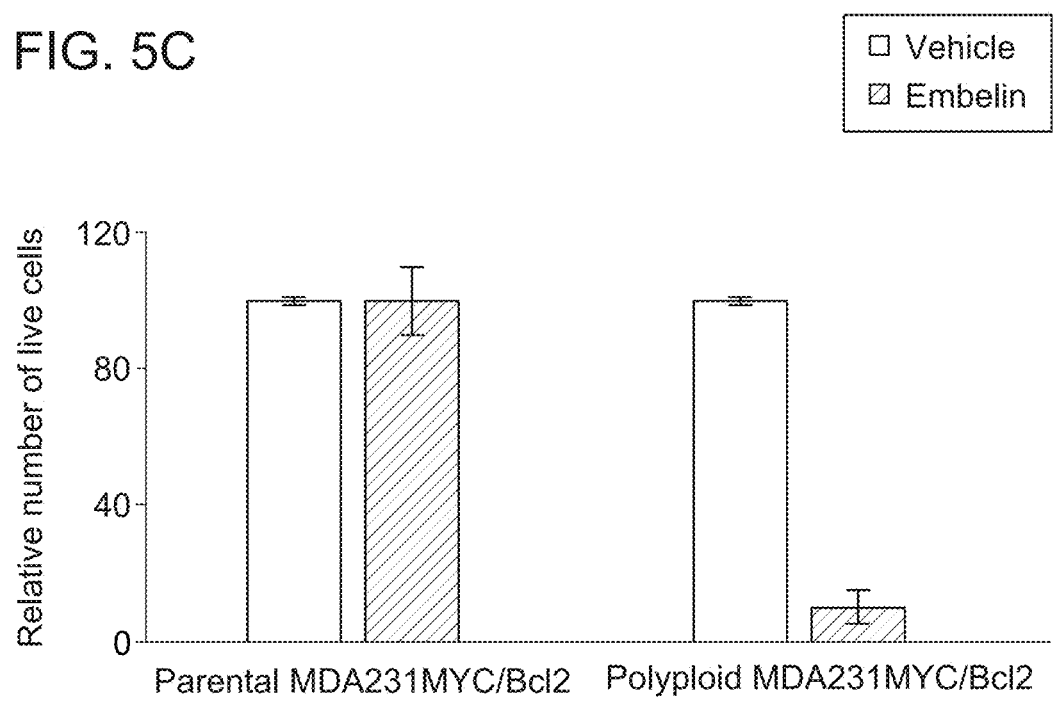

FIG. 6A
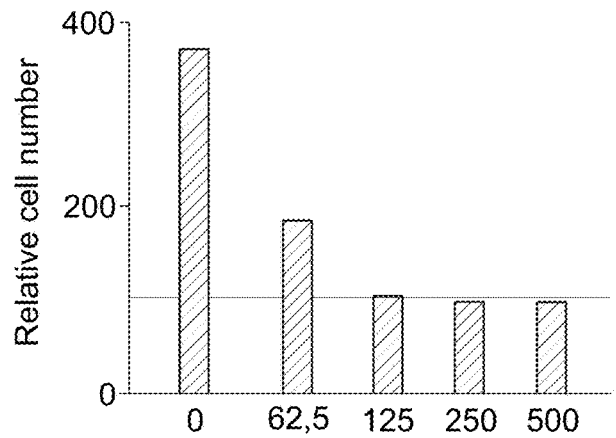
FIG. 6B
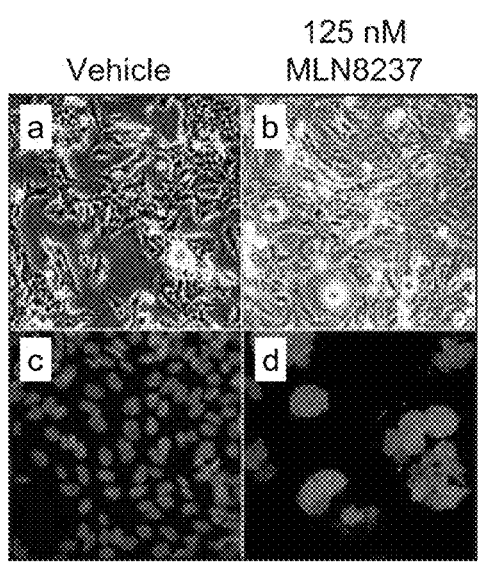
FIG. 6C
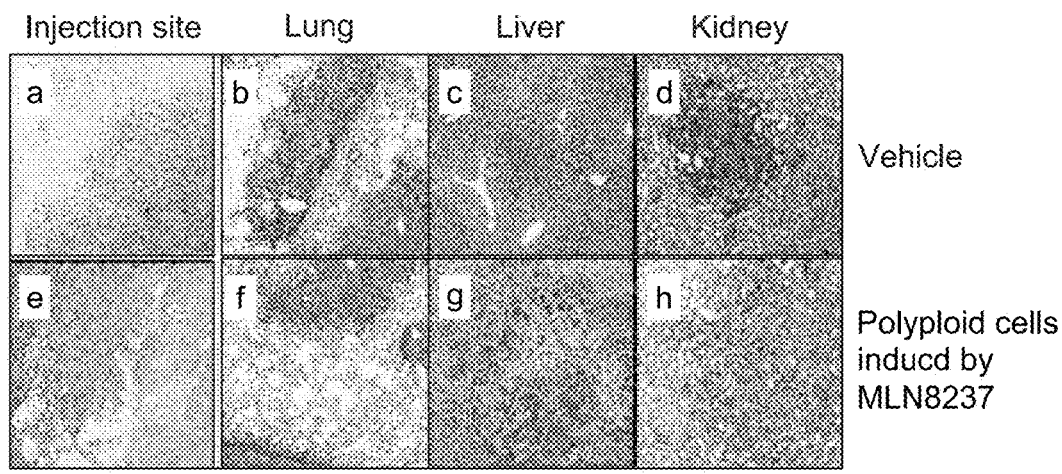
FIG. 6D
Implant into nude mice subcutaneously
0 → 4
Days after initiation of treatment with MLN8237
FIG. 6E
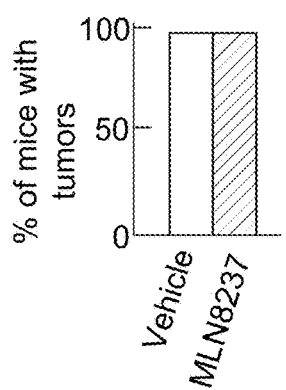
FIG. 6F
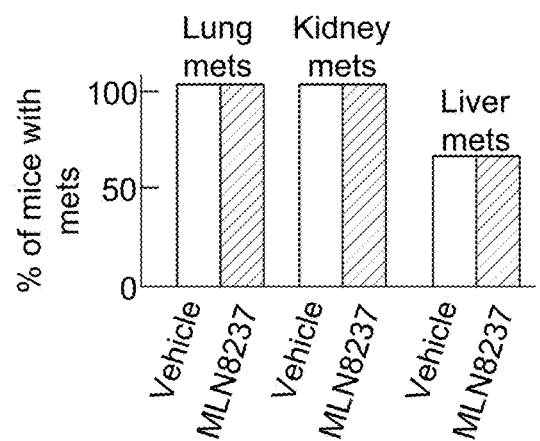

Days after initiation of treatment with MLN8237

CANCER TREATMENT USING COMPOUNDS THAT SELECTIVELY TARGET POLYPLOID CANCER CELLS FOR DISRUPTION

CROSS REFERENCE TO RELATED APPLICATIONS

This application claims the priority benefit under 35 U.S.C § 119 to U.S. Provisional Patent Application Ser. No. 62/513,958, titled "CANCER TREATMENT USING COMPOUNDS THAT SELECTIVELY TARGET POLYPLOID CANCER CELLS FOR DISRUPTION," filed on Jun. 1, 2017, the disclosure of which is hereby incorporated by reference in its entirety for all purposes.

FIELD OF THE INVENTION

The present disclosure generally relates to cancer treatments and more particularly, to compounds and compositions that selectively target polyploid cancer cells for disruption.

BACKGROUND OF THE INVENTION

Tumor evolution, underpinned by the enormous intratumor heterogeneity, represents a formidable obstacle that currently prevents the development of truly curative treatments for cancer. Significantly elevated genomic content in polyploid tumor cells has been proposed to facilitate rapid tumor evolution and the acquisition of therapy resistance in various incurable cancers. Polyploidy is also a hallmark of radiation induced mitotic catastrophe and is a common phenomenon occurring in tumor cells with impaired p53 function following exposure to various cytotoxic, genotoxic and antimitotic agents. There is also an increasing appreciation that cancer cells undergo endoreplication to give rise to polyploidy as a means of survival during mitotic catastrophe or genotoxic stress.

Although polyploidy was previously thought to be incompatible with cellular proliferation, recent data indicate that at low frequency some of these polyploid cancer cells can actually re-enter into mitotic cell cycles via a process of genome reduction called depolyploidization. Furthermore, both preexisting polyploid cells and treatment-induced polyploid cells are capable of tumor formation. These findings suggest that survival from anticancer treatment by endoreplication and subsequent depolyploidization provides a mechanism by which cancer cells become resistance to anti-cancer drugs. It has also been postulated that this mechanism might contribute to the recurrence of more aggressive cancers, because endoreplication may lead to additional oncogenic alterations resulting from repeated rounds of replication in a cell that might have compromised the fidelity of DNA synthesis. Therefore, it is highly desirable to find a way to kill these polyploid tumor cells. Unfortunately, there is currently no effective therapeutic treatment that selectively targets polyploid cells for destruction.

SUMMARY OF THE INVENTION

The disclosure addresses these needs and more through a cell-based screening system that exploits Bcl-2 to protect polyploid cells from both apoptosis and autophagic cell death when MYC-VX680 synthetic lethality is elicited. This innovative system allows for the conversion of a diploid cell line into a homogeneous population of large polyploid cells for the propose of drug screening. After screening a library of natural product extracts in the cell-based system, the natural product embelin was identified from the fruits of *Embelia ribes* Burm as a selective killer of polyploid cells. This embelin activity has not been previously reported in the literature. The therapeutic efficacy of embelin was further demonstrated against tumorigenesis of polyploid cells but not pseudo-diploid cells in vitro and in vivo. The data suggest that embelin and its derivatives, are useful to eliminate polyploid tumor cells and consequently, prevent tumor relapse through a rationale combination with polyploid inducing treatments.

Thus, in one embodiment the disclosure provides a compound of Formula I:

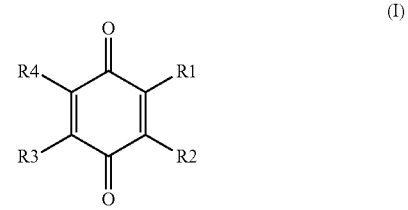

(I)

or a pharmaceutically acceptable salt thereof, wherein:

$R^1$ is independently selected from hydrogen, hydroxyl, amino, thiol, alkyl, alkenyl, alkynyl, cycloalkyl, cycloalkenyl, cycloalkynyl, alkylcycloalkyl, alkylcycloalkenyl, alkylcycloalkynyl, alkyloxy, alkyloxyalkyl, alkylamine, dialkylamine, arylamine, heterocyclyl, alkylheterocyclyl, aryl, alkylaryl, and heteroaryl, each optionally independently substituted with 1 to 6 substituents selected from hydrogen, halogen, nitro, amino, cyano, isocyano, thiol, hydroxyl, alkyl, cycloalkyl, alkoxy, aryloxy esteryl, and aryl;

$R^2$ is independently selected from alkyl, alkenyl, alkynyl, cycloalkyl, alkylcycloalkyl, alkoxy, and alkyloxyalkyl, each optionally independently substituted with 1 to 6 substituents selected from hydrogen, halogen, nitro, amino, cyano, isocyano, thiol, hydroxyl, alkyl, cycloalkyl, alkoxy, aryloxy, esteryl, and aryl;

$R^3$ and $R^4$ are each independently selected from hydrogen, hydroxyl, amino, thiol, alkyl, alkenyl, alkynyl, cycloalkyl, cycloalkenyl, cycloalkynyl, alkylcycloalkyl, alkylcycloalkenyl, alkylcycloalkynyl, alkyloxy, alkyloxyalkyl, alkylamine, dialkylamine, arylamine, heterocyclyl, heterocyclyl, alkylheterocyclyl, aryl, alkylaryl, and heteroaryl, each optionally independently substituted with 1 to 6 substituents selected from hydrogen, halogen, nitro, amino, cyano, isocyano, thiol, hydroxyl, alkyl, cycloalkyl, alkoxy, aryloxy esteryl, or aryl, or $R^3$ and $R^4$, together form a 5 or 6-membered heteroaryl ring or a 6-membered aryl ring, each optionally independently substituted with 1 to 6 substituents selected from hydrogen, halogen, nitro, amino, cyano, isocyano, thiol, hydroxyl, alkyl, cycloalkyl, alkoxy, aryloxy esteryl, or aryl.

In another embodiment, the disclosure provides a method of identifying a compound that selectively kills polyploid cells, by converting a diploid cell line into a homogeneous population of polyploid cells; screening one or more compounds against the homogeneous population of polyploid cells; and identifying a compound that selectively kills the homogeneous population of polyploid cells.

In another embodiment, the disclosure provides a method of killing polyploid tumor cells, by administering to a patient in need thereof, a compound of Formula I or a pharmaceutically acceptable salt thereof, wherein the compound of Formula I and R', $R^2$, $R^3$, and $R^4$ are as described herein.

BRIEF DESCRIPTION OF THE DRAWINGS

The present disclosure, in accordance with one or more various embodiments, is described in detail with reference to the following figures. The drawings are provided for purposes of illustration only and merely depict exemplary embodiments of the disclosure. These drawings are provided to facilitate the reader's understanding of the disclosure and should not be considered limiting of the breadth, scope, size, or applicability of the disclosure. It should be noted that for clarity and ease of illustration these drawings are not necessarily made to scale.

FIG. 1C is a graph which illustrates RPE cells expressing Myc and active Akt;

FIG. 5C is a graph which illustrates embelin selectively killing polyploid breast cancer cells as opposed to diploid cells;

FIG. 6A is a graph which illustrates Aurora kinase inhibitor MLN8237 elicits cytostatic effect on lung cancer cells;

FIG. 6B shows images of cells which illustrates MM-BRAF cells develop polyploidy when exposed to MLN8237;

FIG. 6C shows images of tumors from selected tissues derived from polyploid MM-BRAF cells which illustrates version to small, diploid tumor cells;

FIG. 6D is a diagram which illustrates the experimental design where MM-BRAF cells were induced with MLN8237 in vitro for polyploid cells, followed by subcutaneous implantation into nude mice;

FIG. 6E is a graph which illustrates the percentage of mice with tumors after implantation of polyploid MM-BRAF cells;

FIG. 6F is a graph which illustrates the number of mice with metastatic tumors in the indicated tissues after implantation of polyploid MM-BRAF cells;

DETAILED DESCRIPTION OF EXEMPLARY EMBODIMENTS

Figure 1A:
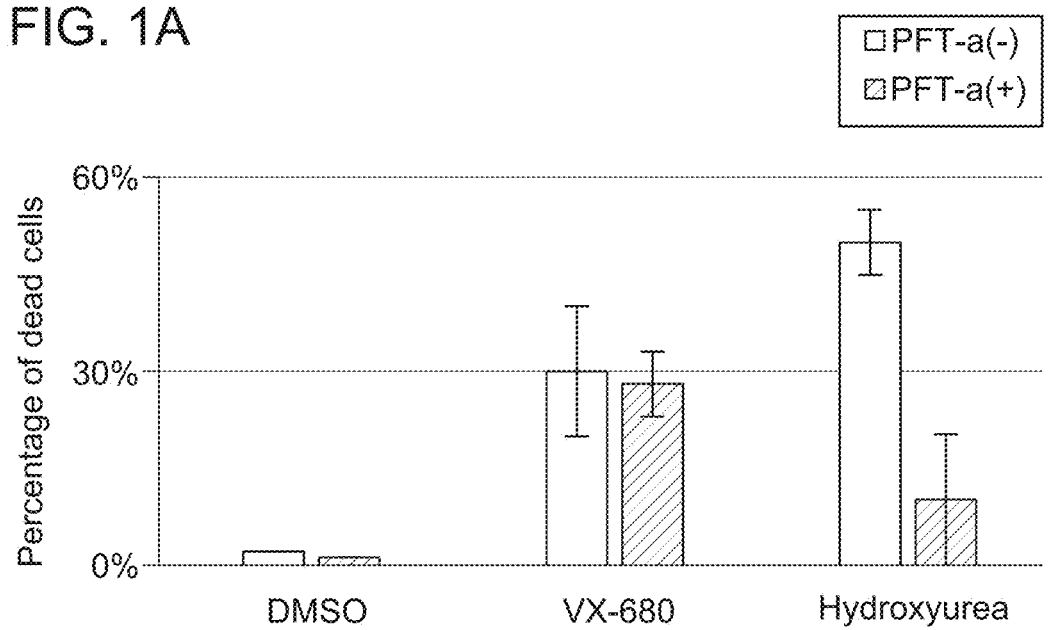
FIG. 1A is a graph which illustrates p53 function in RPE-Myc cells.

The following description is presented to enable a person of ordinary skill in the art to make and use embodiments described herein. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the disclosure. The word "exemplary" is used herein to mean "serving as an example illustration." Any aspect or design described herein as "exemplary" is not necessarily to be construed as preferred or advantageous over other aspects or designs. Thus, the present disclosure is not intended to be limited to the examples described herein and shown but is to be accorded the scope consistent with the claims.

As used herein, reference to any biological drug includes any fragment, modification or variant of the biologic, including any pegylated form, glycosylated form, lipidated form, cyclized form or conjugated form of the biologic or such fragment, modification or variant or prodrug of any of the foregoing. As used herein, reference to any small molecule drug includes any salt, acid, base, hydrate, solvate, ester, isomer, or polymorph thereof or metabolite or prodrug of any of the foregoing.

It should be understood that the specific order or hierarchy of steps in the process disclosed herein is an example of exemplary approaches. Based upon design preferences, it is understood that the specific order or hierarchy of steps in the processes may be rearranged while remaining within the scope of the present disclosure. Any accompanying method claims present elements of the various steps in a sample order and are not meant to be limited to the specific order or hierarchy presented.

Abbreviations used herein have their conventional meaning within the chemical and biological arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e. unbranched) or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds.

Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl".

The term "alkylene" by itself or as part of another substituent means a divalent radical derived from an alkyl, as exemplified, but not limited, by —$CH_2CH_2CH_2CH_2$—, —$CH_2CH=CHCH_2$—, —$CH_2CsCCH_2$—, —$CH_2CH_2CH(CH_2CH_2CH_3)CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or cyclic hydrocarbon radical, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N(CHs)—$CH_3$, —$CH_2$—S—$CH_2$—$CH_3$, —$CH_2$—$CH_{29}$—S(O)—$CH_3$, —$CH_2$—$CH_2$—$S(O)_2$—$CH_3$, —CH=CH—O—$CH_3$, —$Si(CH_3)_3$, —$CH_2$—CH=N—$OCH_3$, —CH=CH—$N(CH_3)$—$CH_3$, —$OCH_3$, —$OCH_2CH_3$, and —CN. Up to two or three heteroatoms may be consecutive, such as, for example, —$CH_2$—NH—$OCH_3$ and —$CH_2$—O—$Si(CH_3)_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxo, alkylenedioxo, alkyleneamino, alkylenediamino, and the like). Still. further, for alkylene and heteroalkylene linking groups, no orientation of the linking group is implied by the direction in which the formula of the linking group is written. For example, the formula —$C(O)OR^1$— represents both —C(O)OR'— and —R'OC(O). As described above, heteroalkyl groups, as used herein, include those groups that are attached to the remainder of the molecule through a heteroatom, such as —C(O)R', —C(O)NR', —NR'R", —OR', —SR', and/or —$SO_2R$'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyi" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyi include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyi and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent radicals of aryl and heteroaryl, respectively.

For brevity, the term "aryl" when used in combination with other terms (e.g., aryloxo, arylthioxo, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" referrers to a carbon or heteroatom.

The term "oxo" as used herein means an oxygen that is double bonded to a carbon atom.

Each of above terms (e.g., "alkyl," "heteroalkyl," "cycloalkyl, and "heterocycloalkyl". "aryl," "heteroaryl" as well as their divalent radical derivatives) are meant to include both substituted and unsubstituted forms of the indicated radical. Preferred substituents for each type of radical are provided below.

Substituents for alkyl, heteroalkyl, cycloalkyl, heterocycloalkyl monovalent and divalent derivative radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR$^1$R$^{11}$R"$^1$, —OC(O)R', —C(O)R", —CO$_2$RVC(O)NR$^1$R", —OC(O)NR$^1$R", —NR$^{11}$C(O)R$^1$, —NR'—C(O)NR"R''', —NR$^{11}$C(O)OR$^1$, —NR—C(NR$^1$R$^1$O=NR$^{1}$", —S(O)R', —S(O)$_2$R', —S(O)$_2$NR$^1$R", —NRSO$_2$R$^1$, —CN and —NO$_2$ in a number ranging from zero to (2 m'+1), where m$^1$ is the total number of carbon atoms in such radical. R', R", R$^{1'1}$ and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the invention includes more than one R group, for example, each of the R groups is independently selected as are each R$^1$, R", R$^{111}$ and R"" groups when more than one of these groups is present. When R$^1$ and R" are attached to the same nitrogen atom, they can be combined with the nitrogen atom to form a A-, 5-, 6-, or 7-membered ring. For example, —NR$^1$R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl radicals above, exemplary substituents for aryl and heteroaryl groups (as well as their divalent derivatives) are varied and are selected from, for example: halogen, —OR$^1$, —NR$^1$R", —SR', -halogen, —SiR$^1$R$^{11}$R$^{11'}$, —OC(O)R', —C(O)R$^1$, —CO$_2$R', —C(O)NR$^1$R", —OC(O)NR$^1$R", —NR$^{11}$C(O)R$^1$, —NR^C(O)NR$^{11}$R''', —NR$^{11}$C(O)OR$^1$, —NR—C(NR$^1$R$^{11}$R$^{11}$O=NR''$^{11}$, —NR—C(NR$^1$R$^1$O=NR$^{1}$", —S(O)R", —S(O)$_2$R', —S(O)$_2$NR$^1$R", —NRSO$_2$R$^1$, —CN and —NO$_2$, —R', —N$_3$, —CH(Ph)$_2$, fluoro(C$_1$-C$_4$)alkoxo, and fluoro(C$_1$-C$_4$)alkyl, in a number ranging from zero to the total number of open valences on aromatic ring system; and where R', R", R''' and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the invention includes more than one R group, for example, each of the R groups is independently selected as are each R', R", R''' and R"" groups when more than one of these groups is present.

Two of the substituents on adjacent atoms of aryl or heteroaryl ring may optionally form a ring of the formula -T-C(O)—(CRR')$_q$-U-, wherein T and U are independently —NR—, —O—, —CRR$^1$— or a single bond, and q is an integer of from 0 to 3. Alternatively, two of the substituents on adjacent atoms of aryl or heteroaryl ring may optionally be replaced with a substituent of the formula -A-(CH$_2$VB-, wherein A and B are independently —CRR$^1$—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of aryl or heteroaryl ring may optionally be replaced with a substituent of the formula —(CRR$^1$)$_s$—X$^1$—(C"R''')d-$_3$ where s and d are independently integers of from 0 to 3, and X$^1$ is —O—, —NR'—, —S—, —S(O)—, —S(O)$_2$—, Or —S(O)$_2$NR$^1$—. The substituents R, R$^1$, R" and R''' are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "heteroatom" or "ring heteroatom" is meant to include oxygen (O), nitrogen (N), sulfur (S), phosphorus (P), and silicon (Si).

An "aminoalkyl" as used herein refers to an amino group covalently bound to an alkylene linker. The amino group is —NR$^1$R", wherein R$^1$ and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

A "substituent group," as used herein, means a group selected from the following moieties:

(A) —OH$_5$—NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroary], and (ii) alkyl, heteroalkyl, cycloalkyl, heterocycloalkyl, aryl, and heteroaryl, substituted with at least one substituent selected from:

(a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein means a group selected from all of the substituents described above for a "substituent group," wherein each substituted or unsubstituted alkyl is a substituted or unsubstituted Cj-C$_{2O}$ alkyl, each substituted or unsubstituted heteroalkyl is a substituted or unsubstituted 2 to 20 membered heteroalkyl, each substituted or unsubstituted cycloalkyl is a substituted or unsubstituted C$_4$-C$_8$ cycloalkyl, and each substituted or unsubstituted heterocycloalkyl is a substituted or unsubstituted 4 to 8 membered heterocycloalkyl.

A "lower substituent" or "lower substituent group," as used herein means a group selected from all of the substituents described above for a "substituent group," wherein each substituted or unsubstituted alkyl is a substituted or unsubstituted C$_1$-Cg alkyl, each substituted or unsubstituted heteroalkyl is a substituted or unsubstituted 2 to 8 membered heteroalkyl, each substituted or unsubstituted cycloalkyl is a substituted or unsubstituted C$_5$-C$_7$ cycloalkyl, and each substituted or unsubstituted heterocycloalkyl is a substituted or unsubstituted 5 to 7 membered heterocycloalkyl.

The compounds of the present invention may exist as salts. The present invention includes such salts. Examples of applicable salt forms include hydrochlorides, hydrobromides, sulfates, methanesulfonates, nitrates, maleates, acetates, citrates, fumarates, tartrates (eg (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents or resolved using conventional techniques. When the compounds described herein contain olefinic bonds or other centers of geometric asymmetry, and unless specified otherwise, it is intended that the compounds include both E and Z geometric isomers.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of atoms that constitute such compounds. For example, the compounds may be radiolabeled with radioactive isotopes, such as for example tritium ($^{3}$H), iodine-125 ($^{125}$I) or carbon-14 ($^{14}$C). All isotopic variations of the compounds of the present invention, whether radioactive or not, are encompassed within the scope of the present invention.

The term "pharmaceutically acceptable salts" is meant to include salts of active compounds which are prepared with relatively nontoxic acids or bases, depending on the particular substituent moieties found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like {see, for example, Berge et ah, "Pharmaceutical Salts", Journal of Pharmaceutical Science, 1977, 66, 1-19). Certain specific compounds of the present invention contain both basic and acidic functionalities that allow the compounds to be converted into either base or acid addition salts.

In addition to salt forms, the present invention provides compounds, which are in a prodrug form. Prodrugs of the compounds described herein are those compounds that readily undergo chemical changes under physiological conditions to. provide the compounds of the present invention.

Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

The terms "a," "an," or "a(n)"} when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

The description of the compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocyclo alkyl or heteroaryl is attached to the remainder of the molecule via a ring heteroatom in compliance with principles of chemical bonding known to those skilled in the art thereby avoiding inherently unstable compounds.

The terms "treating" or "treatment" in reference to a particular disease includes prevention of the disease.

The symbol—~ denotes the point of attachment of a moiety to the remainder of the molecule.

As used herein, the phrase "polyploidy inducing agent' refers to a therapeutic compound of any type (e.g., nonselective or selective), including small molecules, antibodies, antisense oligonucleotides, small interfering RNAs, microRNA-based compounds that induce polyploidy in one or more cells. Methods for determining the induction or evidence of polyploidy in one or more cells can be obtained using routine techniques known in the art. For example, evidence of polyploidy can be determined by detecting elevated expression of p53. p53 is a surrogate for polyploidization in cells harboring wildtype p53 (See, Gizatullin, F. et al., "The Aurora Kinase inhibitor VX-680 induces endoreduplication and apoptosis preferentially in cells with compromised p53-dependent postmitotic checkpoint function." Cancer Res. 66, 7668-77. (2006)). Additionally, cells in which polyploidy has been induced exhibit a gross morphological increase in cell size and multinucleation, both of which can be detected using routine techniques known in the art.

Examples of polyploidy inducing agents, include, but are not limited to, Aurora Kinase inhibitors, microtubule inhibitors (such as, for example, Taxotere, Vincristine, nocodazole, paclitaxel or colcemid), pan-kinase inhibitors (such as, for example, staurosporine), oncolytic viruses (such as, for example, ONYX-015), Acridine orange, Dolastain-10, Noscapine, topoisomerase II inhibitors (such as, for example, ICRF-187 or ICRF-193), 2-4-(7-chloro-2-quinoxalinyl) oxyphenoxypropionic acid, 2-4-(7-bromo-2-quinolinyl)oxyphenoxypropionic acid, Platycodin D, microtubule poisons (such as, for example, JG-03-14), actin polymerization inhibitors (such as, for example, Cytochalasin B), Bistramide A or antitumor antibiotics (Such as, for example, Mithramycin SKI).

As used herein, an "Aurora Kinase inhibitor" refers to a therapeutic compound of any type (e.g., non-selective or selective), including small molecules, antibodies, antisense oligos, small interfering RNA, or microRNA-based compounds, that suppresses the activity of at least one member of the Aurora Kinase family, which includes Aurora A, Aurora B, and Aurora C.

The methods of the present disclosure are useful with any known or hereafter developed Aurora Kinase A inhibitor. Examples of an Aurora Kinase A inhibitor are PHA-73.9358, MLN-8054, R-763, JNJ-7706621, MP-529 and MP-235.

The methods of the present disclosure are useful with any known or hereafter developed Aurora Kinase B inhibitor. Examples of an Aurora Kinase B inhibitor are AZD1152, ZM447439, VX-680/MK0457 and Hesperadin. AZD1152, also known as, 2-3-(4-(5-2-(3-Fluorophenyl)amino-2-oxoethyl)-1H-pyrazol-3-yl)aminoquinazolin-7yl)oxy)propyl) (ethyl)-aminoethyl dihydrogen phosphate, is a prodrug of a pyrazoloquinazoline Aurora Kinase inhibitor (AZD1152-hydroxyquinazoline pyrazolanilide (HQPA)) and is converted rapidly to the active AZD1152-HQPA in plasma (See, Mortlock, A A. et al., J. Med. Chem., 50:2213-24 (2007)). AZD1152-HQPA is a highly potent and selective inhibitor of Aurora B. ZM447439, also known as 4-(4-(N-benzoylamino) anilino)-6-methoxy-7-(3-(1-morpholino)propoxy) guinaZoline, is a quinazoline derivative, inhibits Aurora A and Aurora B. VX-680/MK0457 is a cyclopropane carboxylic acid of {4-4-(4-methyl-piperazin-1-yl)-6-(5-methyl-2H-pyrazol-3-ylamino)-pyrimidin-2-ylsulphanyl-phenylamide and inhibits Aurora A, Aurora B and Aurora C. Hesperadin, an indolinone, inhibits Aurora B.

The methods of the present disclosure are useful with any known or hereafter developed Aurora Kinase C inhibitor. Examples of an Aurora Kinase C inhibitor are AZD1152 and VX-680/MK-0457.

Frequently induced by a variety of anticancer treatments, polyploidy is known to confer tumor cells with multi-drug resistance and is believed to be responsible for tumor relapse. Currently, there are not any clinically approved anticancer drugs that can target polyploid tumor cells for elimination.

To address these needs, the disclosure provides a cell-based assay to screen for small molecules that can selectively kill polyploid tumor cells, as opposed to their parental pseudo-diploid cells. Applying an extract library of natural products to the screening assay, the hydroxybenzoquinone known as embelin, isolated from the fruits of *Embelia ribes* Burm, was identified as a selective agent against polyploid tumor cells. In three different tumor types tested, embelin triggered the rapid demise of polyploid cancer cells but not their parental pseudo-diploid cells in each cell line in vitro. In all three cases, embelin also suppressed tumorigenesis of polyploid cancer cells but not their parental cells in vivo. Collectively, this data reveals a previously unknown lethal activity of embelin selectively against polyploid cells, pioneering the concept that the combination of polyploid-inducing treatment with embelin or one of its derivatives, could be a viable strategy for the treatment of a variety of human cancers, and provide the first example of a therapeutic drug combination that specifically exploits polyploidization.

Accordingly, in one embodiment the disclosure provides a compound of Formula I:

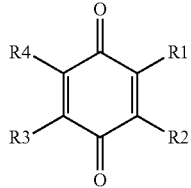
(I)

or a pharmaceutically acceptable salt thereof, wherein:

$R^1$ is independently selected from hydrogen, hydroxyl, amino, thiol, alkyl, alkenyl, alkynyl, cycloalkyl, cycloalkenyl, cycloalkynyl, alkylcycloalkyl, alkylcycloalkenyl, alkylcycloalkynyl, alkyloxy, alkyloxyalkyl, alkylamine, dialkylamine, arylamine, heterocyclyl, alkylheterocyclyl, aryl, alkylaryl, and heteroaryl, each optionally independently substituted with 1 to 6 substituents selected from hydrogen, halogen, nitro, amino, cyano, isocyano, thiol, hydroxyl, alkyl, cycloalkyl, alkoxy, aryloxy esteryl, and aryl;

$R^2$ is independently selected from alkyl, alkenyl, alkynyl, cycloalkyl, alkylcycloalkyl, alkoxy, and alkyloxyalkyl, each optionally independently substituted with 1 to 6 substituents selected from hydrogen, halogen, nitro, amino, cyano, isocyano, thiol, hydroxyl, alkyl, cycloalkyl, alkoxy, aryloxy, esteryl, and aryl;

$R^3$ and $R^4$ are each independently selected from hydrogen, hydroxyl, amino, thiol, alkyl, alkenyl, alkynyl, cycloalkyl, cycloalkenyl, cycloalkynyl, alkylcycloalkyl, alkylcycloalkenyl, alkylcycloalkynyl, alkyloxy, alkyloxyalkyl, alkylamine, dialkylamine, arylamine, heterocyclyl, heterocyclyl, alkylheterocyclyl, aryl, alkylaryl, and heteroaryl, each optionally independently substituted with 1 to 6 substituents selected from hydrogen, halogen, nitro, amino, cyano, isocyano, thiol, hydroxyl, alkyl, cycloalkyl, alkoxy, aryloxy esteryl, or aryl, or $R^3$ and $R^4$ together form a 5 or 6-membered heteroaryl ring or a 6-membered aryl ring, each optionally independently substituted with 1 to 6 substituents selected from hydrogen, halogen, nitro, amino, cyano, isocyano, thiol, hydroxyl, alkyl, cycloalkyl, alkoxy, aryloxy esteryl, or aryl.

In another embodiment, the disclosure provides a compound of Formula I, wherein:

$R^1$ is independently selected from hydrogen, hydroxyl, amino, thiol, $(C_1-C_{20})$alkyl, $(C_2-C_{20})$alkenyl, $(C_2-C_{20})$alkynyl, $(C_3-C_{20})$cycloalkyl, $(C_5-C_{20})$cycloalkenyl, $(C_8-C_{20})$cycloalkynyl, $(C_1-C_{20})$alkyl$(C_3-C_{20})$cycloalkyl, $(C_1-C_{20})$alkyl$(C_5-C_{20})$cyclo-alkenyl, $(C_1-C_{20})$alkyl$(C_8-C_{20})$cycloalkynyl, $(C_1-C_{20})$alkyloxy, $(C_1-C_{20})$alkyloxy$(C_1-C_{20})$alkyl, $(C_1-C_{20})$alkylamine, $(C_1-C_{20})$dialkylamine, arylamine, heterocyclyl, $(C_1-C_{20})$alkylhetero-cyclyl, aryl, $(C_1-C_{20})$alkylaryl, and heteroaryl, each optionally independently substituted with 1 to 6 substituents selected from hydrogen, halogen, nitro, amino, cyano, isocyano, thiol, hydroxyl, $(C_1-C_6)$alkyl, $(C_3-C_{20})$cycloalkyl, $(C_1-C_{20})$alkoxy, aryloxy, esteryl, and aryl;

$R^2$ is independently selected from $(C_1-C_{20})$alkyl, $(C_2-C_{20})$alkenyl, $(C_2-C_{20})$alkynyl, $(C_3-C_{20})$cycloalkyl, $(C_1-C_{20})$alkyl$(C_3-C_{20})$cycloalkyl, $(C_1-C_{20})$alkoxy, and $(C_1-C_{20})$alkyloxy$(C_1-C_{20})$alkyl, each optionally independently substituted with 1 to 6 substituents selected from hydrogen, halogen, nitro, amino, cyano, isocyano, thiol, hydroxyl, $(C_1-C_{20})$alkyl, $(C_3-C_{20})$cycloalkyl, $(C_1-C_{20})$alkoxy, aryloxy, esteryl, and aryl;

$R^3$ and $R^4$ are each independently selected from hydrogen, hydroxyl, amino, thiol, $(C_1-C_{20})$alkyl, $(C_2-C_{20})$alkenyl, $(C_2-C_{20})$alkynyl, $(C_3-C_{20})$cycloalkyl, $(C_5-C_{20})$cycloalkenyl, $(C_8-C_{20})$cycloalkynyl, $(C_1-C_{20})$alkyl$(C_3-C_{20})$cycloalkyl, $(C_1-C_{20})$alkyl$(C_5-C_{20})$cycloalkenyl, $(C_1-C_{20})$alkyl$(C_8-C_{20})$cycloalkynyl, $(C_1-C_{20})$alkyloxy, $(C_1-C_{20})$alkyloxy$(C_1-C_{20})$alkyl, $(C_1-C_{20})$alkylamine, $(C_1-C_{20})$dialkylamine, arylamine, heterocyclyl, alkylheterocyclyl, aryl, alkylaryl, and heteroaryl, each optionally independently substituted with 1 to 6 substituents selected from hydrogen, halogen, nitro, amino, cyano, isocyano, thiol, hydroxyl, $(C_1-C_{20})$alkyl, $(C_3-C_{20})$cycloalkyl, $(C_1-C_{20})$alkoxy, aryloxy, esteryl, and aryl, or $R^3$ and $R^4$ together form a 5 or 6-membered heterocyclic or heteroaryl ring or a 6-membered aryl ring, each optionally independently substituted with 1 to 6 substituents selected from hydrogen, halogen, nitro, amino, cyano, isocyano, thiol, hydroxyl, $(C_1-C_{20})$alkyl, $(C_3-C_{20})$cycloalkyl, $(C_1-C_{20})$alkoxy, aryloxy, esteryl, and aryl.

In another embodiment, the disclosure provides a compound of Formula I, wherein:

$R^3$ and $R^4$ together form a 5-membered heterocyclic ring selected from substituted or unsubstituted pyrrolidine, substituted or unsubstituted pyrazolidine, substituted or unsubstituted imidazolidine, substituted or unsubstituted tetrahydrofuran, and substituted or unsubstituted tetrahydrothiophene, or $R^3$ and $R^4$ together form a 5-membered heteroaryl ring selected from substituted or unsubstituted furan, substituted or unsubstituted thiophene, substituted or unsubstituted oxazole, substituted or unsubstituted isoxazole, substituted or unsubstituted indole, substituted or unsubstituted benzofuran, and substituted or unsubstituted benzo[b]thiophene, or $R^3$ and $R^4$ together form a 6-membered heterocyclic ring selected from substituted or unsubstituted piperidine, substituted or unsubstituted piperazine, substituted or unsubstituted thiane, substituted or unsubstituted morpholine, and substituted or unsubstituted thiomorpholine, or $R^3$ and $R^4$ together form a 6-membered heteroaryl ring selected from substituted or unsubstituted pyridine, substituted or unsubstituted pyridazine, substituted or unsubstituted pyrimidine, substituted or unsubstituted pyrazine, and substituted or unsubstituted morpholine, or $R^3$ and $R^4$ together form a 6-membered aryl ring selected from substituted or unsubstituted phenyl, substituted or unsubstituted biphenyl, and substituted or unsubstituted naphthyl.

In another embodiment, the disclosure provides a compound of Formula I, wherein:

$R^1$ is independently selected from hydroxyl;
$R^2$ is independently selected from $(C_1-C_{20})$alkyl;
$R^3$ is independently selected from hydroxyl; and
$R^4$ is independently selected from hydrogen.

In another embodiment, the disclosure provides a method of identifying a compound that selectively kills polyploid cells, by:

converting a diploid cell line into a homogeneous population of polyploid cells;

screening one or more compounds against the homogeneous population of polyploid cells; and identifying a compound that selectively kills the homogeneous population of polyploid cells.

In another embodiment, the disclosure provides a method of identifying a compound that selectively kills polyploid cells, further including: exploiting Bcl-2 to protect the homogeneous population of polyploid cells from apoptosis and/or autophagic cell death when MYC-VX680 synthetic lethality is elicited.

In another embodiment, the disclosure provides a method of identifying a compound that selectively kills polyploid cells, wherein the one or more compounds has Formula I:

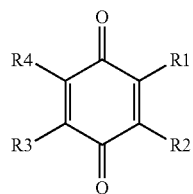

or a pharmaceutically acceptable salt thereof, wherein:

$R^1$ is independently selected from hydrogen, hydroxyl, amino, thiol, alkyl, alkenyl, alkynyl, cycloalkyl, cycloalkenyl, cycloalkynyl, alkylcycloalkyl, alkylcycloalkenyl, alkylcycloalkynyl, alkyloxy, alkyloxyalkyl, alkylamine, dialkylamine, arylamine, heterocyclyl, alkylheterocyclyl, aryl, alkylaryl, and heteroaryl, each optionally independently substituted with 1 to 6 substituents selected from hydrogen, halogen, nitro, amino, cyano, isocyano, thiol, hydroxyl, alkyl, cycloalkyl, alkoxy, aryloxy esteryl, and aryl;

$R^2$ is independently selected from alkyl, alkenyl, alkynyl, cycloalkyl, alkylcycloalkyl, alkoxy, and alkyloxyalkyl, each optionally independently substituted with 1 to 6 substituents selected from hydrogen, halogen, nitro, amino, cyano, isocyano, thiol, hydroxyl, alkyl, cycloalkyl, alkoxy, aryloxy, esteryl, and aryl;

$R^3$ and $R^4$ are each independently selected from hydrogen, hydroxyl, amino, thiol, alkyl, alkenyl, alkynyl, cycloalkyl, cycloalkenyl, cycloalkynyl, alkylcycloalkyl, alkylcycloalkenyl, alkylcycloalkynyl, alkyloxy, alkyloxyalkyl, alkylamine, dialkylamine, arylamine, heterocyclyl, heterocyclyl, alkylheterocyclyl, aryl, alkylaryl, and heteroaryl, each optionally independently substituted with 1 to 6 substituents selected from hydrogen, halogen, nitro, amino, cyano, isocyano, thiol, hydroxyl, alkyl, cycloalkyl, alkoxy, aryloxy esteryl, or aryl, or $R^3$ and $R^4$ together form a 5 or 6-membered heteroaryl ring or a 6-membered aryl ring, each optionally independently substituted with 1 to 6 substituents selected from hydrogen, halogen, nitro, amino, cyano, isocyano, thiol, hydroxyl, alkyl, cycloalkyl, alkoxy, aryloxy esteryl, or aryl.

In another embodiment, the disclosure provides a method of identifying a compound that selectively kills polyploid cells, wherein:

$R^1$ is independently selected from hydrogen, hydroxyl, amino, thiol, $(C_1-C_{20})$alkyl, $(C_2-C_{20})$alkenyl, $(C_2-C_{20})$alkynyl, $(C_3-C_{20})$cycloalkyl, $(C_5-C_{20})$cycloalkenyl, $(C_8-C_{20})$cycloalkynyl, $(C_1-C_{20})$alkyl$(C_3-C_{20})$cycloalkyl, $(C_1-C_{20})$alkyl$(C_5-C_{20})$cyclo-alkenyl, $(C_1-C_{20})$alkyl$(C_8-C_{20})$cycloalkynyl, $(C_1-C_{20})$alkyloxy, $(C_1-C_{20})$alkyloxy$(C_1-C_{20})$alkyl, $(C_1-C_{20})$alkylamine, $(C_1-C_{20})$dialkylamine, arylamine, heterocyclyl, $(C_1-C_{20})$alkylhetero-cyclyl, aryl, $(C_1-C_{20})$alkylaryl, and heteroaryl, each optionally independently substituted with 1 to 6 substituents selected from hydrogen, halogen, nitro, amino, cyano, isocyano, thiol, hydroxyl, $(C_1-C_6)$alkyl, $(C_3-C_{20})$cycloalkyl, $(C_1-C_{20})$alkoxy, aryloxy, esteryl, and aryl;

$R^2$ is independently selected from $(C_1-C_{20})$alkyl, $(C_2-C_{20})$alkenyl, $(C_2-C_{20})$alkynyl, $(C_3-C_{20})$cycloalkyl, $(C_1-C_{20})$alkyl$(C_3-C_{20})$cycloalkyl, $(C_1-C_{20})$alkoxy, and $(C_1-C_{20})$alkyloxy$(C_1-C_{20})$alkyl, each optionally independently substituted with 1 to 6 substituents selected from hydrogen, halogen, nitro, amino, cyano, isocyano, thiol, hydroxyl, $(C_1-C_{20})$alkyl, $(C_3-C_{20})$cycloalkyl, $(C_1-C_{20})$alkoxy, aryloxy, esteryl, and aryl;

$R^3$ and $R^4$ are each independently selected from hydrogen, hydroxyl, amino, thiol, $(C_1-C_{20})$alkyl, $(C_2-C_{20})$alkenyl, $(C_2-C_{20})$alkynyl, $(C_3-C_{20})$cycloalkyl, $(C_5-C_{20})$cycloalkenyl, $(C_8-C_{20})$cycloalkynyl, $(C_1-C_{20})$alkyl$(C_3-C_{20})$cycloalkyl, $(C_1-C_{20})$alkyl$(C_5-C_{20})$cycloalkenyl, $(C_1-C_{20})$alkyl$(C_8-C_{20})$cycloalkynyl, $(C_1-C_{20})$alkyloxy, $(C_1-C_{20})$alkyloxy$(C_1-C_{20})$alkyl, $(C_1-C_{20})$alkylamine, $(C_1-C_{20})$dialkylamine, arylamine, heterocyclyl, alkylheterocyclyl, aryl, alkylaryl, and heteroaryl, each optionally independently substituted with 1 to 6 substituents selected from hydrogen, halogen, nitro, amino, cyano, isocyano, thiol, hydroxyl, $(C_1-C_{20})$alkyl, $(C_3-C_{20})$cycloalkyl, $(C_1-C_{20})$alkoxy, aryloxy, esteryl, and aryl, or $R^3$ and $R^4$ together form a 5 or 6-membered heterocyclic or heteroaryl ring or a 6-membered aryl ring, each optionally independently substituted with 1 to 6 substituents selected from hydrogen, halogen, nitro, amino, cyano, isocyano, thiol, hydroxyl, $(C_1-C_{20})$alkyl, $(C_3-C_{20})$cycloalkyl, $(C_1-C_{20})$alkoxy, aryloxy, esteryl, and aryl.

In another embodiment, the disclosure provides a method of identifying a compound that selectively kills polyploid cells, wherein:

$R^3$ and $R^4$ together form a 5-membered heterocyclic ring selected from substituted or unsubstituted pyrrolidine, substituted or unsubstituted pyrazolidine, substituted or unsubstituted imidazolidine, substituted or unsubstituted tetrahydrofuran, and substituted or unsubstituted tetrahydrothiophene, or $R^3$ and $R^4$ together form a 5-membered heteroaryl ring selected from substituted or unsubstituted furan, substituted or unsubstituted thiophene, substituted or unsubstituted oxazole, substituted or unsubstituted isoxazole, substituted or unsubstituted indole, substituted or unsubstituted benzofuran, and substituted or unsubstituted benzo[b]thiophene, or $R^3$ and $R^4$ together form a 6-membered heterocyclic ring selected from substituted or unsubstituted piperidine, substituted or unsubstituted piperazine, substituted or unsubstituted thiane, substituted or unsubstituted morpholine, and substituted or unsubstituted thiomorpholine, or $R^3$ and $R^4$ together form a 6-membered heteroaryl ring selected from substituted or unsubstituted pyridine, substituted or unsubstituted pyridazine, substituted or unsubstituted pyrimidine, substituted or unsubstituted pyrazine, and substituted or unsubstituted morpholine, or $R^3$ and $R^4$ together form a 6-membered aryl ring selected from substituted or unsubstituted phenyl, substituted or unsubstituted biphenyl, and substituted or unsubstituted naphthyl.

In another embodiment, the disclosure provides a method of identifying a compound that selectively kills polyploid cells, wherein:

$R^1$ is independently selected from hydroxyl;
$R^2$ is independently selected from $(C_1-C_{20})$alkyl;
$R^3$ is independently selected from hydroxyl; and
$R^4$ is independently selected from hydrogen.

In another embodiment, the disclosure provides a method of killing polyploid tumor cells by administering to a patient in need thereof, a compound of Formula I:

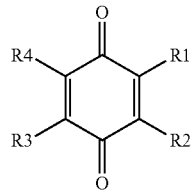

or a pharmaceutically acceptable salt thereof, wherein:

$R^1$ is independently selected from hydrogen, hydroxyl, amino, thiol, alkyl, alkenyl, alkynyl, cycloalkyl, cycloalkenyl, cycloalkynyl, alkylcycloalkyl, alkylcycloalkenyl, alkylcycloalkynyl, alkyloxy, alkyloxyalkyl, alkylamine, dialkylamine, arylamine, heterocyclyl, alkylheterocyclyl, aryl, alkylaryl, and heteroaryl, each optionally independently substituted with 1 to 6 substituents selected from hydrogen, halogen, nitro, amino, cyano, isocyano, thiol, hydroxyl, alkyl, cycloalkyl, alkoxy, aryloxy esteryl, and aryl;

$R^2$ is independently selected from alkyl, alkenyl, alkynyl, cycloalkyl, alkylcycloalkyl, alkoxy, and alkyloxyalkyl, each optionally independently substituted with 1 to 6 substituents selected from hydrogen, halogen, nitro, amino, cyano, isocyano, thiol, hydroxyl, alkyl, cycloalkyl, alkoxy, aryloxy, esteryl, and aryl;

$R^3$ and $R^4$ are each independently selected from hydrogen, hydroxyl, amino, thiol, alkyl, alkenyl, alkynyl, cycloalkyl, cycloalkenyl, cycloalkynyl, alkylcycloalkyl, alkylcycloalkenyl, alkylcycloalkynyl, alkyloxy, alkyloxyalkyl, alkylamine, dialkylamine, arylamine, heterocyclyl, heterocyclyl, alkylheterocyclyl, aryl, alkylaryl, and heteroaryl, each optionally independently substituted with 1 to 6 substituents selected from hydrogen, halogen, nitro, amino, cyano, isocyano, thiol, hydroxyl, alkyl, cycloalkyl, alkoxy, aryloxy esteryl, or aryl, or $R^3$ and $R^4$ together form a 5 or 6-membered heteroaryl ring or a 6-membered aryl ring, each optionally independently substituted with 1 to 6 substituents selected from hydrogen, halogen, nitro, amino, cyano, isocyano, thiol, hydroxyl, alkyl, cycloalkyl, alkoxy, aryloxy esteryl, or aryl.

In another embodiment, the disclosure provides a method of killing polyploid tumor cells wherein:

$R^1$ is independently selected from hydrogen, hydroxyl, amino, thiol, $(C_1$-$C_{20})$alkyl, $(C_2$-$C_{20})$alkenyl, $(C_2$-$C_{20})$alkynyl, $(C_3$-$C_{20})$cycloalkyl, $(C_5$-$C_{20})$cycloalkenyl, $(C_1$-$C_{20})$cycloalkynyl, $(C_1$-$C_{20})$alkyl$(C_3$-$C_{20})$cycloalkyl, $(C_1$-$C_{20})$alkyl $(C_5$-$C_{20})$cyclo-alkenyl, $(C_1$-$C_{20})$alkyl$(C_5$-$C_{20})$cycloalkynyl, $(C_1$-$C_{20})$alkyloxy, $(C_1$-$C_{20})$alkyloxy$(C_1$-$C_{20})$alkyl, $(C_1$-$C_{20})$alkylamine, $(C_1$-$C_{20})$dialkylamine, arylamine, heterocyclyl, $(C_1$-$C_{20})$alkylhetero-cyclyl, aryl, $(C_1$-$C_{20})$alkylaryl, and heteroaryl, each optionally independently substituted with 1 to 6 substituents selected from hydrogen, halogen, nitro, amino, cyano, isocyano, thiol, hydroxyl, $(C_1$-$C_6)$alkyl, $(C_3$-$C_{20})$cycloalkyl, $(C_1$-$C_{20})$alkoxy, aryloxy, esteryl, and aryl;

$R^2$ is independently selected from $(C_1$-$C_{20})$alkyl, $(C_2$-$C_{20})$alkenyl, $(C_2$-$C_{20})$alkynyl, $(C_3$-$C_{20})$cycloalkyl, $(C_1$-$C_{20})$alkyl $(C_3$-$C_{20})$cycloalkyl, $(C_1$-$C_{20})$alkoxy, and $(C_1$-$C_{20})$alkyloxy $(C_1$-$C_{20})$alkyl, each optionally independently substituted with 1 to 6 substituents selected from hydrogen, halogen, nitro, amino, cyano, isocyano, thiol, hydroxyl, $(C_1$-$C_{20})$alkyl, $(C_3$-$C_{20})$cycloalkyl, $(C_1$-$C_{20})$alkoxy, aryloxy, esteryl, and aryl;

$R^3$ and $R^4$ are each independently selected from hydrogen, hydroxyl, amino, thiol, $(C_1$-$C_{20})$alkyl, $(C_2$-$C_{20})$alkenyl, $(C_2$-$C_{20})$alkynyl, $(C_3$-$C_{20})$cycloalkyl, $(C_5$-$C_{20})$cycloalkenyl, $(C_8$-$C_{20})$cycloalkynyl, $(C_1$-$C_{20})$alkyl$(C_3$-$C_{20})$cycloalkyl, $(C_1$-$C_{20})$alkyl$(C_5$-$C_{20})$cycloalkenyl, $(C_1$-$C_{20})$alkyl$(C_8$-$C_{20})$ cycloalkynyl, $(C_1$-$C_{20})$alkyloxy, $(C_1$-$C_{20})$alkyloxy$(C_1$-$C_{20})$ alkyl, $(C_1$-$C_{20})$alkylamine, $(C_1$-$C_{20})$dialkylamine, arylamine, heterocyclyl, alkylheterocyclyl, aryl, alkylaryl, and heteroaryl, each optionally independently substituted with 1 to 6 substituents selected from hydrogen, halogen, nitro, amino, cyano, isocyano, thiol, hydroxyl, $(C_1$-$C_{20})$alkyl, $(C_3$-$C_{20})$cycloalkyl, $(C_1$-$C_{20})$alkoxy, aryloxy, esteryl, and aryl, or $R^3$ and $R^4$ together form a 5 or 6-membered heterocyclic or heteroaryl ring or a 6-membered aryl ring, each optionally independently substituted with 1 to 6 substituents selected from hydrogen, halogen, nitro, amino, cyano, isocyano, thiol, hydroxyl, $(C_1$-$C_{20})$alkyl, $(C_3$-$C_{20})$cycloalkyl, $(C_1$-$C_{20})$ alkoxy, aryloxy, esteryl, and aryl.

In another embodiment, the disclosure provides a method of killing polyploid tumor cells wherein:

$R^3$ and $R^4$ together form a 5-membered heterocyclic ring selected from substituted or unsubstituted pyrrolidine, substituted or unsubstituted pyrazolidine, substituted or unsubstituted imidazolidine, substituted or unsubstituted tetrahydrofuran, and substituted or unsubstituted tetrahydrothiophene, or $R^3$ and $R^4$ together form a 5-membered heteroaryl ring selected from substituted or unsubstituted furan, substituted or unsubstituted thiophene, substituted or unsubstituted oxazole, substituted or unsubstituted isoxazole, substituted or unsubstituted indole, substituted or unsubstituted benzofuran, and substituted or unsubstituted benzo[b]thiophene, or $R^3$ and $R^4$ together form a 6-membered heterocyclic ring selected from substituted or unsubstituted piperidine, substituted or unsubstituted piperazine, substituted or unsubstituted thiane, substituted or unsubstituted morpholine, and substituted or unsubstituted thiomorpholine, or $R^3$ and $R^4$ together form a 6-membered heteroaryl ring selected from substituted or unsubstituted pyridine, substituted or unsubstituted pyridazine, substituted or unsubstituted pyrimidine, substituted or unsubstituted pyrazine, and substituted or unsubstituted morpholine, or $R^3$ and $R^4$ together form a 6-membered aryl ring selected from substituted or unsubstituted phenyl, substituted or unsubstituted biphenyl, and substituted or unsubstituted naphthyl.

In another embodiment, the disclosure provides a method of killing polyploid tumor cells, wherein:

$R^1$ is independently selected from hydroxyl;

$R^2$ is independently selected from $(C_1$-$C_{20})$alkyl;

$R^3$ is independently selected from hydroxyl; and $R^4$ is independently selected from hydrogen.

In another embodiment, the disclosure provides a combination of therapeutic agents for use in treating a patient suffering from cancer, which includes:

a) at least one polyploidy inducing agent for use in inducing polyploidization in one or more cancer cells in the patient; and b) a compound of Formula I:

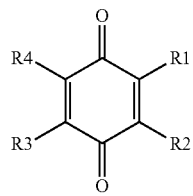

(I)

or a pharmaceutically acceptable salt thereof, wherein:

$R^1$ is independently selected from hydrogen, hydroxyl, amino, thiol, alkyl, alkenyl, alkynyl, cycloalkyl, cycloalkenyl, cycloalkynyl, alkylcycloalkyl, alkylcycloalkenyl, alkylcycloalkynyl, alkyloxy, alkyloxyalkyl, alkylamine, dialkylamine, arylamine, heterocyclyl, alkylheterocyclyl, aryl, alkylaryl, and heteroaryl, each optionally independently substituted with 1 to 6 substituents selected from hydrogen, halogen, nitro, amino, cyano, isocyano, thiol, hydroxyl, alkyl, cycloalkyl, alkoxy, aryloxy esteryl, and aryl;

$R^2$ is independently selected from alkyl, alkenyl, alkynyl, cycloalkyl, alkylcycloalkyl, alkoxy, and alkyloxyalkyl, each optionally independently substituted with 1 to 6 substituents selected from hydrogen, halogen, nitro, amino, cyano, isocyano, thiol, hydroxyl, alkyl, cycloalkyl, alkoxy, aryloxy, esteryl, and aryl;

$R^3$ and $R^4$ are each independently selected from hydrogen, hydroxyl, amino, thiol, alkyl, alkenyl, alkynyl, cycloalkyl, cycloalkenyl, cycloalkynyl, alkylcycloalkyl, alkylcycloalkenyl, alkylcycloalkynyl, alkyloxy, alkyloxyalkyl, alkylamine, dialkylamine, arylamine, heterocyclyl, heterocyclyl, alkylheterocyclyl, aryl, alkylaryl, and heteroaryl, each optionally independently substituted with 1 to 6 substituents selected from hydrogen, halogen, nitro, amino, cyano, isocyano, thiol, hydroxyl, alkyl, cycloalkyl, alkoxy, aryloxy esteryl, or aryl, or $R^3$ and $R^4$ together form a 5 or 6-membered heteroaryl ring or a 6-membered aryl ring, each optionally independently substituted with 1 to 6 substituents selected from hydrogen, halogen, nitro, amino, cyano, isocyano, thiol, hydroxyl, alkyl, cycloalkyl, alkoxy, aryloxy esteryl, or aryl.

In another embodiment, the disclosure provides a combination of therapeutic agents for use in treating a patient suffering from cancer, wherein the at least one polyploidy inducing agent is an Aurora Kinase inhibitor that is specific to one type of aurora kinases or nonspecific to all three types of aurora kinases.

In another embodiment, the disclosure provides a method of treating a patient suffering from cancer, which includes:

a) administering to a patient suffering from cancer a therapeutically effective amount of at least one polyploidy inducing agent, and b) administering to the patient a therapeutically effective amount of a compound of Formula I:

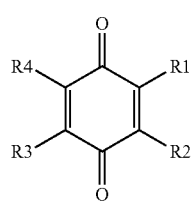

(I)

or a pharmaceutically acceptable salt thereof, wherein:

$R^1$ is independently selected from hydrogen, hydroxyl, amino, thiol, alkyl, alkenyl, alkynyl, cycloalkyl, cycloalkenyl, cycloalkynyl, alkylcycloalkyl, alkylcycloalkenyl, alkylcycloalkynyl, alkyloxy, alkyloxyalkyl, alkylamine, dialkylamine, arylamine, heterocyclyl, alkylheterocyclyl, aryl, alkylaryl, and heteroaryl, each optionally independently substituted with 1 to 6 substituents selected from hydrogen, halogen, nitro, amino, cyano, isocyano, thiol, hydroxyl, alkyl, cycloalkyl, alkoxy, aryloxy esteryl, and aryl;

$R^2$ is independently selected from alkyl, alkenyl, alkynyl, cycloalkyl, alkylcycloalkyl, alkoxy, and alkyloxyalkyl, each optionally independently substituted with 1 to 6 substituents selected from hydrogen, halogen, nitro, amino, cyano, isocyano, thiol, hydroxyl, alkyl, cycloalkyl, alkoxy, aryloxy, esteryl, and aryl;

$R^3$ and $R^4$ are each independently selected from hydrogen, hydroxyl, amino, thiol, alkyl, alkenyl, alkynyl, cycloalkyl, cycloalkenyl, cycloalkynyl, alkylcycloalkyl, alkylcycloalkenyl, alkylcycloalkynyl, alkyloxy, alkyloxyalkyl, alkylamine, dialkylamine, arylamine, heterocyclyl, heterocyclyl, alkylheterocyclyl, aryl, alkylaryl, and heteroaryl, each optionally independently substituted with 1 to 6 substituents selected from hydrogen, halogen, nitro, amino, cyano, isocyano, thiol, hydroxyl, alkyl, cycloalkyl, alkoxy, aryloxy esteryl, or aryl, or $R^3$ and $R^4$ together form a 5 or 6-membered heteroaryl ring or a 6-membered aryl ring, each optionally independently substituted with 1 to 6 substituents selected from hydrogen, halogen, nitro, amino, cyano, isocyano, thiol, hydroxyl, alkyl, cycloalkyl, alkoxy, aryloxy esteryl, or aryl.

In another embodiment, the disclosure provides a method of treating a patient suffering from cancer, wherein the at least one polyploidy inducing agent is an Aurora Kinase inhibitor.

Previously, a synthetic lethal interaction was found that allows the selective killing of cells that overexpress the Myc oncoprotein by pharmaceutical inhibitors of mitotic kinases, some of which are already in clinical trials. This synthetic lethal interaction is attributable to the inhibition of aurora-B kinase, with consequent disabling of the chromosomal passenger protein complex and ensuing DNA endoduplication; and executed by sequential apoptosis and autophagy. The results cast new light on how such inhibitors kill cells, identify overexpression of Myc as a potential biomarker for tumor sensitivity to the inhibitors, and suggest a therapeutic strategy that could mitigate current limitations on both the mitotic inhibitors as therapeutic agents and Myc as a therapeutic target.

It is conceivable that certain oncogenic alterations might modify the synthetic lethal interaction, rendering it less effective in killing of tumor cells. Therefore, polyploid cells induced by the synthetic lethal interaction might survive and accumulate, offering an invaluable model system to screen for drugs that can selectively disrupt polyploid cells as opposed diploid cells. This hypothesis was pursued by testing oncogenic elements that have been well known to promote survival in response to various stress stimuli.

Oncogenic alterations such as mutations/deletion of p53, overproduction of Bcl2 and IAPs, and constitutively active signaling from Ras and Akt have been associated with apoptosis-resistance of tumor cells to chemotherapeutic drugs. These alterations are known to attenuate MYC-dependent apoptosis under various conditions, act synergistically with Myc to elicit malignant transformation and are frequently found in human malignancies with deregulated expression of MYC. Whether these oncogenic alterations have any impact on the MYC-dependent lethality elicited by aurora kinase inhibitor VX-680 in RPE-MYC cells was addressed in a published study using a model cell line to demonstrate MYC-VX680 synthetic lethality.

Figure 1B:
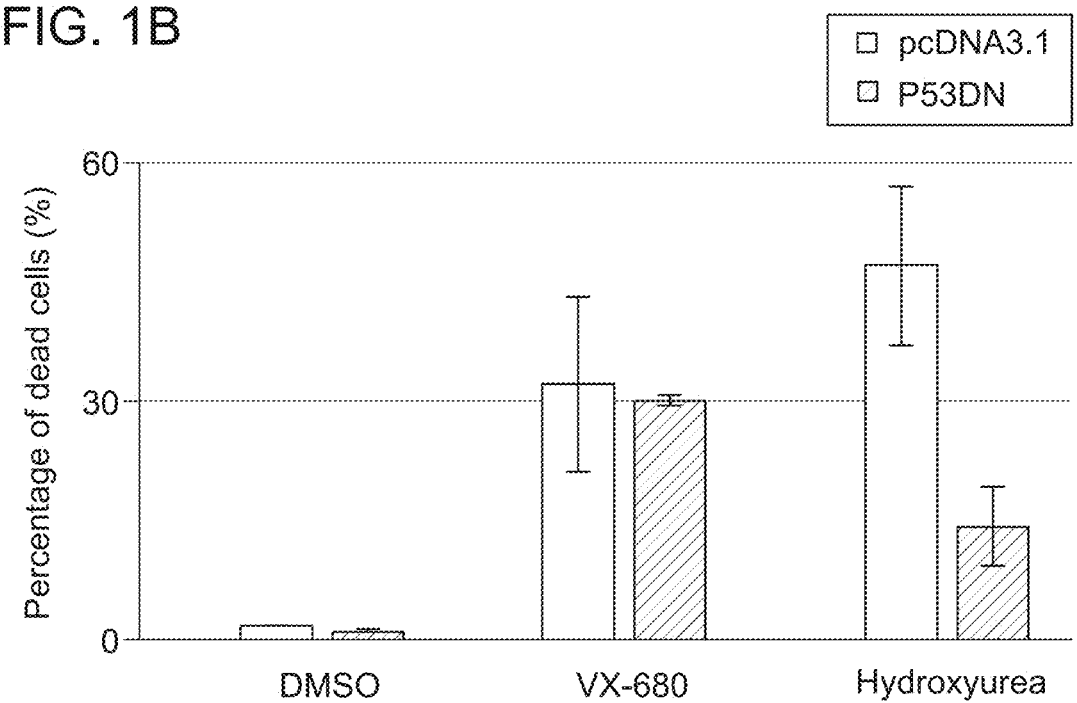
FIG. 1B is a graph which illustrates p53 function in RPE-Myc cells.

The p53 function in RPE-Myc cells can be interfered with by either a small molecule inhibitor of p53, PFT-a, (FIG. 1A), or a dominant negative p53 mutant (FIG. 1B). Neither of these reagents protected RPE-MYC cells from VX-680-induced cell death (FIG. 1A-B). In contrast, either of these reagents conferred more than 70% protection against the cytotoxicity elicited by hydroxyurea (FIG. 1A-B), confirming that the p53 function was compromised. The conclusion was that p53 was not required for the apoptosis elicited by VX-680 in cells overexpressing MYC.

Survival signals are often mediated by the Ras-PI3K-Akt pathway. Overexpression of an active Hu-Ras$^{V12}$ elicited profound senescence in RPE-MYC cells, prevented generation of stable cell lines expressing Hu-Ras$^{V12}$, but were able to generate RPE-MYC cells expressing an active allele of MyrAkt. RPE cells expressing both Myc and active Akt were moderately more sensitive to the cytotoxicity of VX-680 than cells expressing Myc alone (FIG. 1C). Thus, active signaling from Akt enhanced, rather than blocked, the apoptosis elicited by VX-680. The BCL family antiapoptotic factor Bcl2 is a critical regulator of mitochondrion-dependent apoptotic pathway by inhibiting cytochrome C release from mitochondria, whereas XIAP, the most characterized member of the IAP family, has been known to sequester and inactivate active caspases, proteases responsible for apoptosis. The overexpression of Bcl2 or Bcl-xL provided more than 40% protection against the cytotoxicity of VX-680 six days after administration of VX-680 (see, FIGS. 1C and 2) and that overexpression of XIAP has no effect on the MYC-dependent cytotoxicity (FIG. 1C). Since the apoptosis elicited by VX-680 in cells overexpressing MYC was p53-independent and could not be effectively prevented by overexpression of antiapoptotic factors XIAP and an active Akt, the conclusion is that the MYC-dependent cytotoxicity elicited by VX-680 was likely mechanistically distinct from the previously reported MYC-dependent apoptosis in response to hypoxia, growth factor deprivation and genotoxic chemotherapeutic drugs.

Atg6/Beclin1 is part of a protein-kinase complex that participates in formation of autophagosomes. Atg6 is highly induced by Myc-VX680 synthetic lethal interaction and is required for execution of the delayed autophagic death. Since the proteins Bcl-2 and Bcl-x$_L$ suppress autophagy through their interactions with Atg6, suppression of MYC-VX680 synthetic lethality by Bcl-2 and Bcl-xL was tested to see if it was mediated by its interaction with Beclin 1.

Figure 2A:
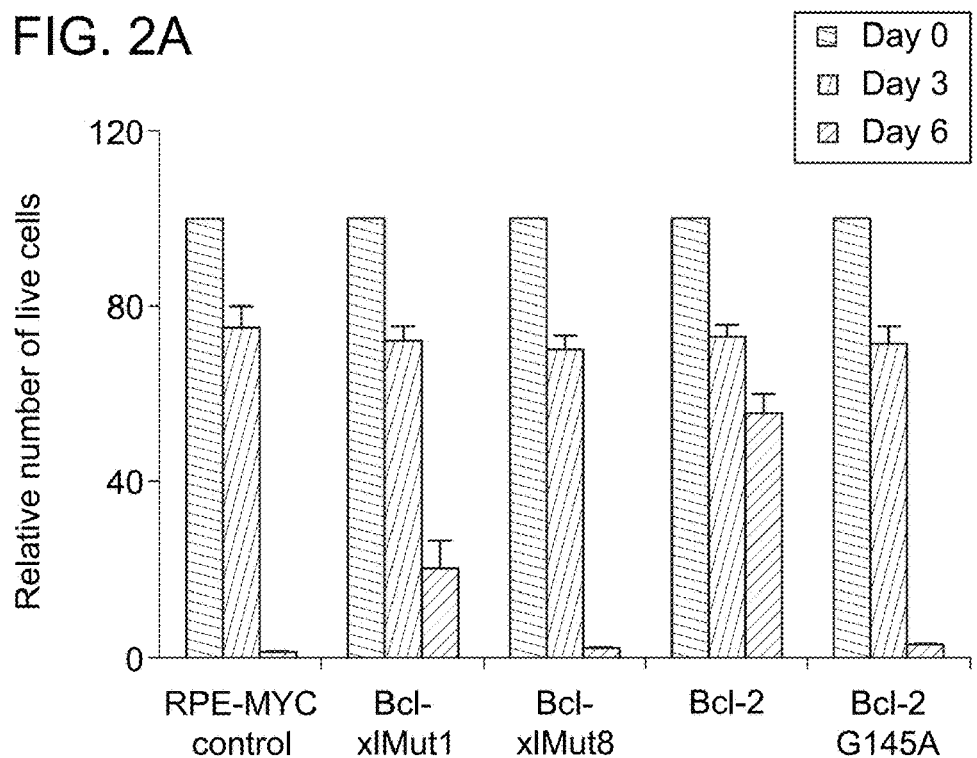
FIG. 2A is a graph which illustrates anti-apoptotic members of the Bcl-2 family confer resistance to MYC-VX680 lethality independent of its anti-apoptotic activity.
Figure 2B:
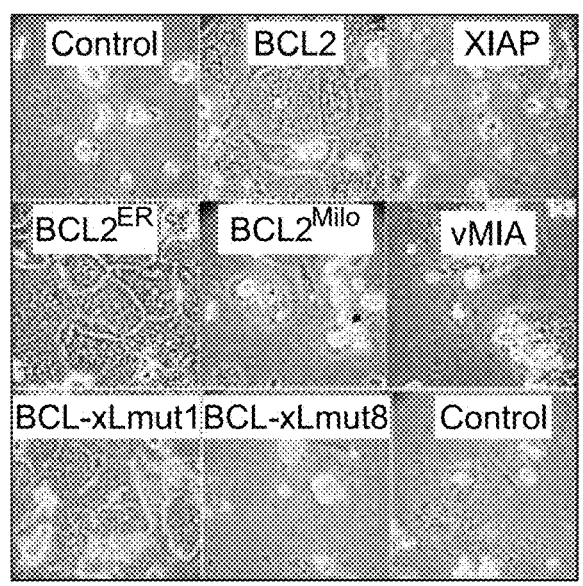
FIG. 2B are images of cells which illustrates anti-apoptotic members of the Bcl-2 family enhancing survival of polyploid RPEMYC cells elicited by VX680.

Wild-type Bcl-2 largely prevented delayed death of multinucleated RPE-MYC cells (FIG. 1C and FIG. 2A-B). Furthermore, expression of a Bcl-x$_L$ mutant 1 (F131V, D133A) that is defective in binding to pro-apoptotic members of the Bcl-2 family, such as Bax, Bak and Bim, suppressed the death of multinucleated cells, indicating that the antiapoptotic function of Bcl-x$_L$ is not required for rescuing multinucleated cells from death (FIG. 2A-C).

Figure 2C:
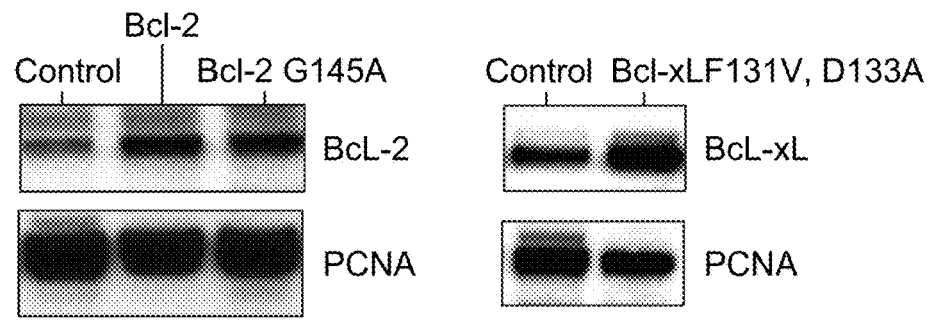
FIG. 2C are western blots which illustrates overexpression of Bcl-2, Bcl-2 G145A and Bcl-xLmut1 in RPE-MYC cells.

By contrast, expression of a Bcl-2 mutant that fails to bind to Beclin 1, Bcl-2 G145, was inert in this rescue experiment (FIG. 2A-B), despite similar levels of expression as wild-type Bcl-2 (FIG. 2C). Thus, a direct interaction with Atg6 was apparently required for Bcl-2 to suppress nonapoptotic cell death of polyploid cells elicited by VX-680. In addition, a Bcl2 derivative that localizes to endoreticulum (Bcl2-ER) but not a version of Bcl2 that localizes to mitochondria (Bcl-2Mito) suppressed the delayed cell death, allowing accumulation of polyploid cells six days after initiation of VX680 treatment (FIG. 2B). Thus, suppression of Myc-VX680 synthetic lethality by Bcl-2 requires its interaction with Atg6 and localization to ER. This Bcl2Beclin1 interaction likely occurs at ER.

Figure 3A:
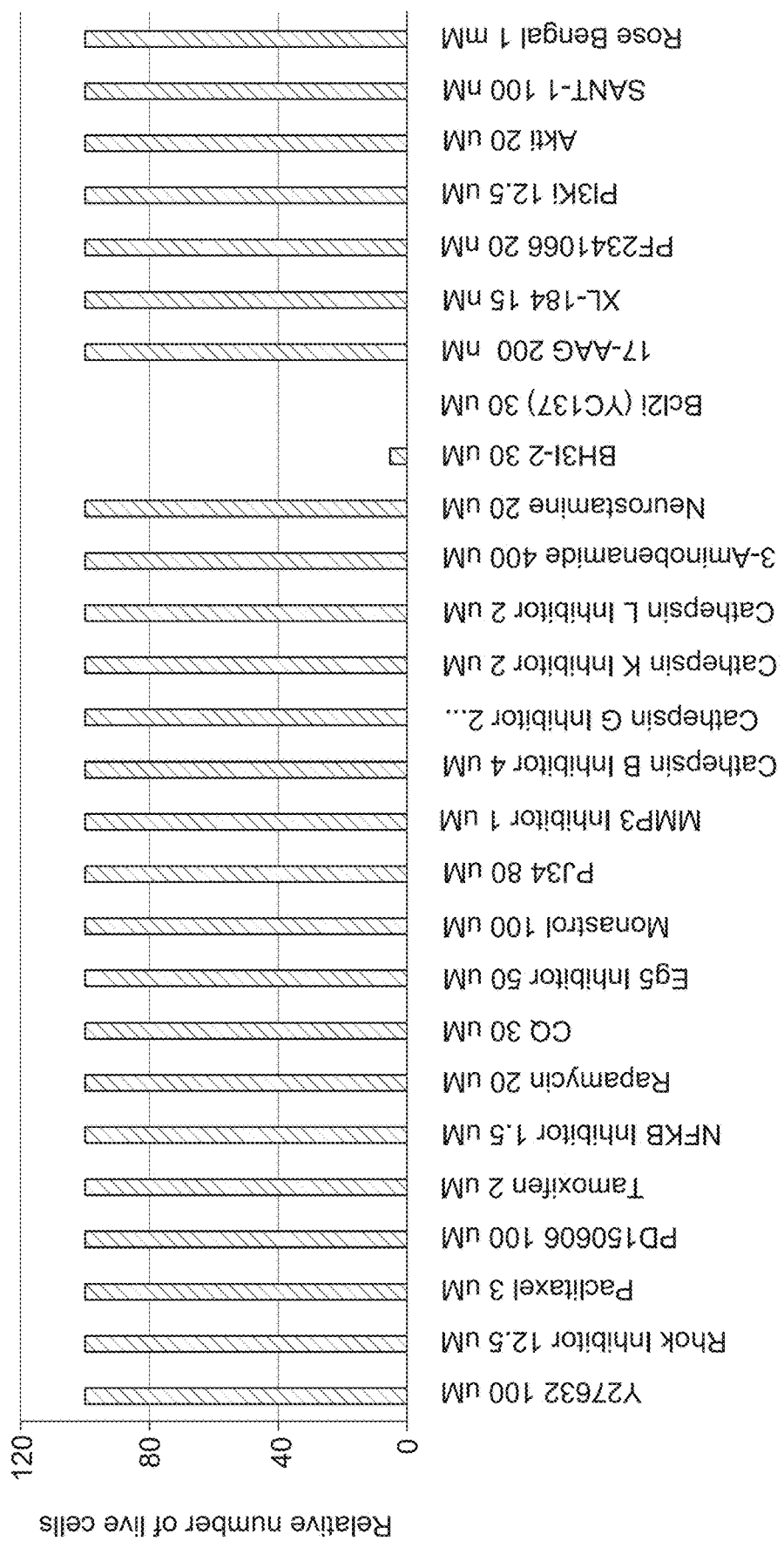
FIG. 3A is a graph which illustrates the effect of various small molecule drugs (Bcl2 inhibitors) on the viability of polyploid cells.

Polyploidy is known to be associated with drug resistance. But currently, there are no drugs in clinical trials that can kill polyploid cells. Since polyploid cells elicited by Myc-VX680 synthetic lethality do not die in the presence of Bcl-2, these cells provide a useful model system to screen for small-molecule drugs that can selectively kill polyploid cells versus diploid cells. The VX680-resistant cell line was named as RPEMYC/Bcl2. As a proof of concept experiment, polyploid RPEMYC/Bcl2 cells induced by VX680 were tested with a panel of 27 small molecule drugs including two Bcl-2 inhibitors. As expected all polyploid cells died within 48 hours of cells exposure to either of the two Bcl-2 inhibitors (FIG. 3A).

Figure 3B:
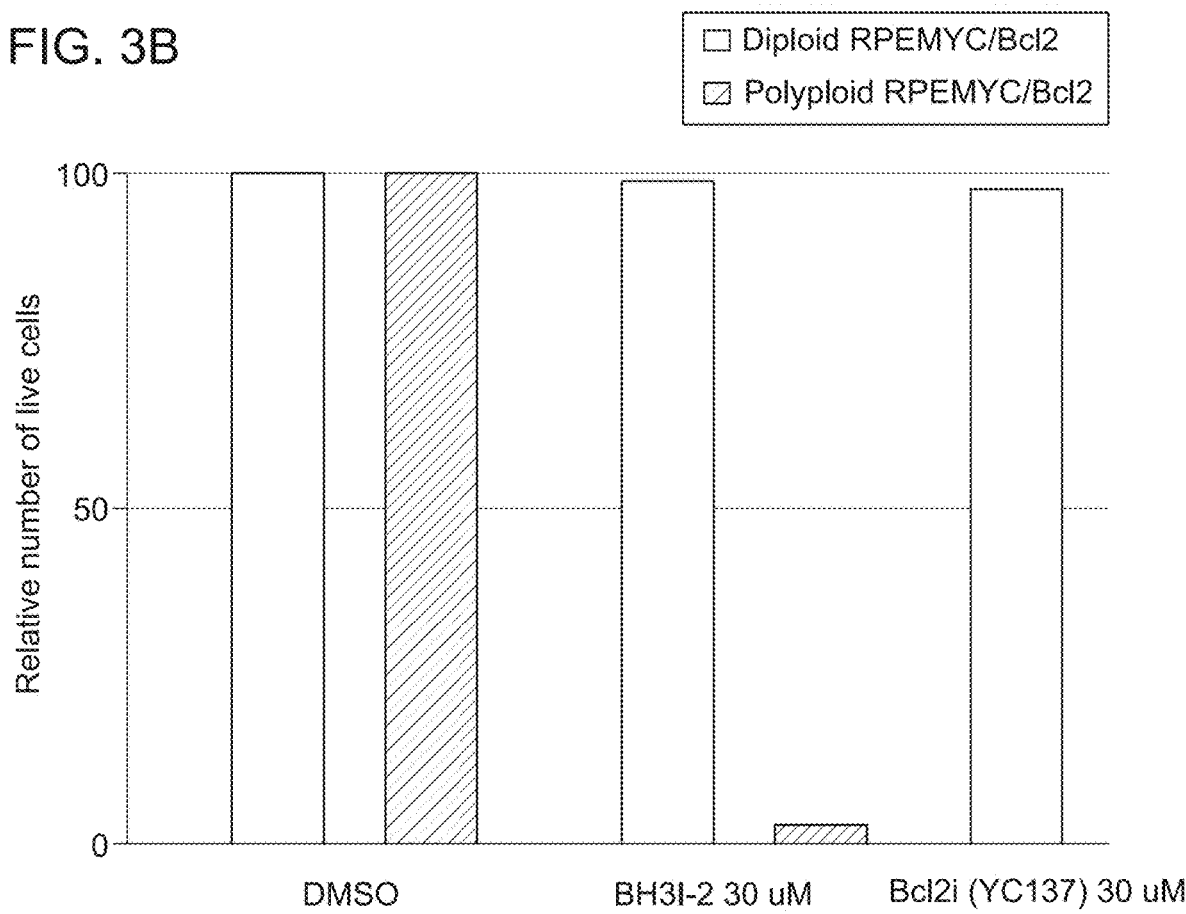
FIG. 3B is a graph which illustrates Bcl2 inhibitors selectively kills polyploid cells as opposed to diploid cells.
Figure 4A:
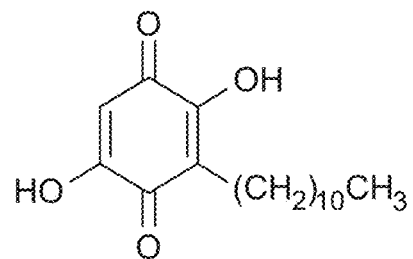
FIG. 4A is a drawing which illustrates the chemical structure of embelin.
Figure 4B:
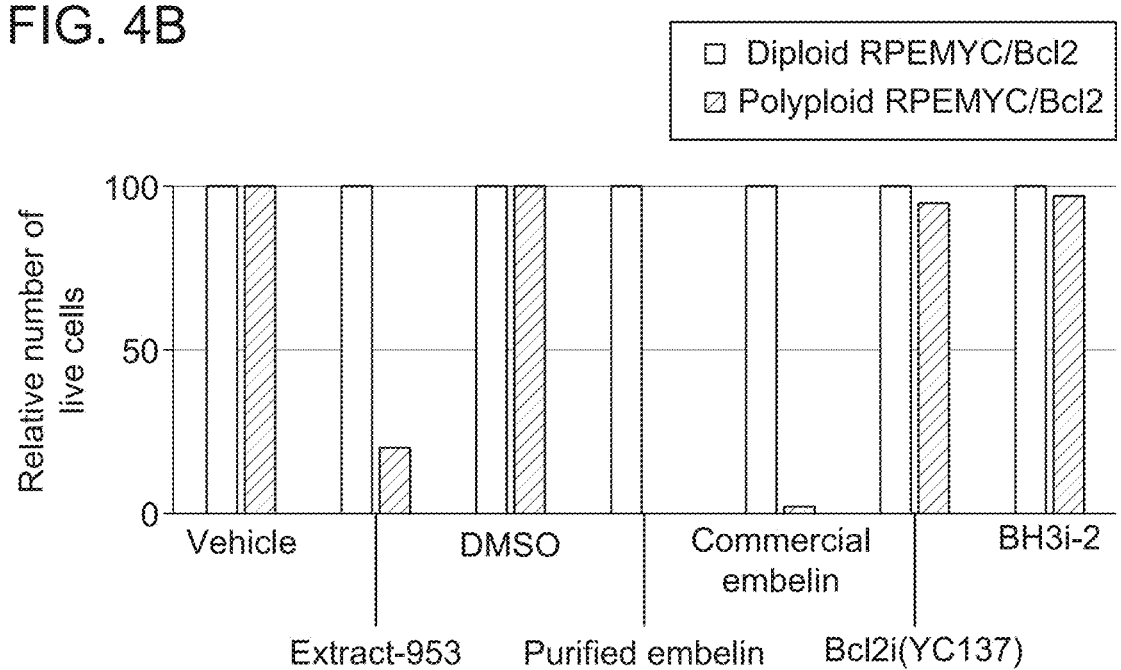
FIG. 4B is a graph which illustrates embelin eliciting polyploidy-selective lethal activity as opposed to diploid cells.

By contrast, all diploid parental RPEMYC/Bcl2 cells survived the treatment (FIG. 3B). For the remaining 25 drugs, none of them elicited death of polyploid RPEMYC/Bcl2 cells (FIG. 3A). This model system was expected to allow the identification of other Bcl-2 inhibitors or inhibitors that block a function either upstream or downstream of Bcl-2. For this purpose, a library of 5000 extracts from 1000 different Chinese medicinal herbs was established. One crude extract was identified that demonstrated potent killing of polyploid cells. Fractionation of the bioactive ingredient in the extracts led to identification of hydroxybenzoquinone embelin (FIG. 4A). The selectively killing was also reproduced with commercially available embelin from Sigma (FIG. 4B). This killing by embelin was much more potent than Bcl2 inhibitors and eliminated most of polyploid cells within 24-hour of treatment (FIG. 4B). In contrast, Bcl2 inhibitors failed to kill any polyploid cells within 24-hour of treatment (FIG. 4B), despite massive cell death occurred after 48 hours (FIG. 3A). A three-fold increase of Bcl2 inhibitor dose also failed to elicit any death of polyploid cells within 24 hours.

This contrast between embelin and Bcl2 inhibitors indicates that embelin might elicit cell death in a mechanism different from that utilized by Bcl2 inhibitors. The killing was not due to inhibition of the known embelin target XIAP either, because depletion of XIAP with its esiRNA did not affect viability of the polyploid cells. Currently, the exact mechanism underlying the killing of embelin is not known. The preliminary data point to the possibility that compromising oxidative phosphorylation of mitochondria by embelin is responsible for the massive disruption of polyploid tumor cells.

Figure 5A:
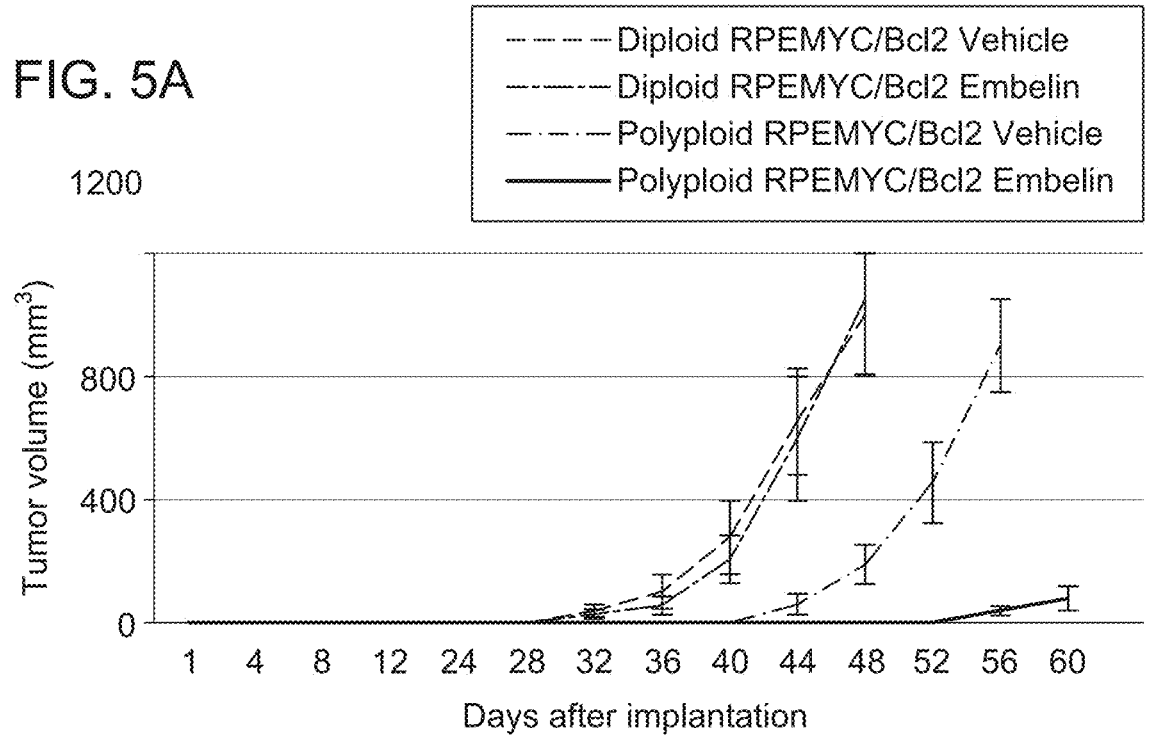
FIG. 5A is a graph which illustrates suppression of tumorigenesis of polyploid RPEMYC/Bcl2 cells by embelin.
Figure 5B:
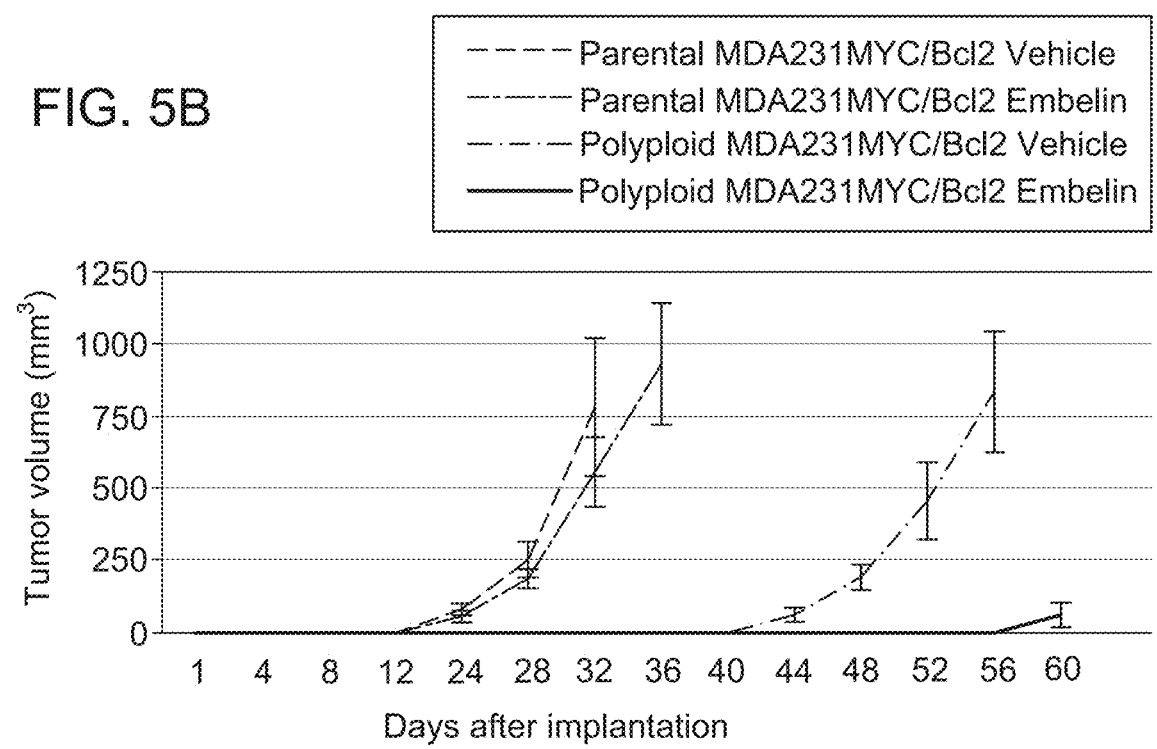
FIG. 5B is a graph which illustrates suppression of tumorigenesis of polyploid breast cancer cells by embelin.

RPEMYC/BCL-2 is a human model cell line that has been transformed by three defined oncogenic elements (Telomerase, Myc and Bcl-2). The cell line could form xenograft tumors in athymic mice. Likewise, polyploid RPEMYC/BCL2 cells induced by VX-680 in vitro can also readily form tumors upon implantation into athymic mice. The therapeutic efficacy of embelin was compared against tumorigenesis of polyploid and diploid RPEMYC/BCL2 cells. The treatment with embelin was initiated immediately after the implantation. This treatment dramatically delayed tumor formation of VX680 induced polyploid cells (FIG. 5A). However, tumorigenesis initiated by parental RPEMYC/BCL2 cells was largely unaffected (FIG. 5A). A similar conclusion was reached with a breast cancer cell line MDA23MYC/Bcl2 that has been engineered to express both MYC and Bcl2. Tumorigenesis of VX680-induced polyploid but not their parental MDA231MYC/Bcl2 cells was delayed by the treatment with embelin (FIG. 5B). The therapeutic efficacy could be attributed to selectively killing of polyploid MDA231MYC/Bcl2 cells, rather than their parental cells (FIG. 5C).

Lung cancer cell line MM-BRAF can form tumors with 100% penetrance at the injection site of athymic mice and metastasize to various internal organs such as liver, lung, kidney and spleen with 70-100% penetrance. Despite MM-BRAF having abundant expression of Myc, these tumor cells were intrinsically resistant to MYC-VX680 synthetic lethality and failed to undergo cell death when exposed to VX-680 in vitro (FIG. 6A). Instead, all cells became multinucleated and polyploid after treatment with VX680 for 4 days (FIG. 6B). The mechanism underlying the VX680 resistance has not yet been explored. These treatment-induced polyploid cells, like untreated parental cells, exhibited a very high frequency of tumor formation and metastasis (FIG. 6C-F). Implantation of just 3000 polyploid cells were sufficient to form primary tumors at the injection site and initiate metastasis to various internal organs including the liver, lung and kidneys. Histologically, tumors formed by both polyploid cells and their parental cells were composed of small cells, rather than large polyploid cells (FIG. 6C). The conclusion is that polyploid MM-BRAF cells have a very high frequency to revert back into diploid cells and re-enter cell division.

Figure 7A:
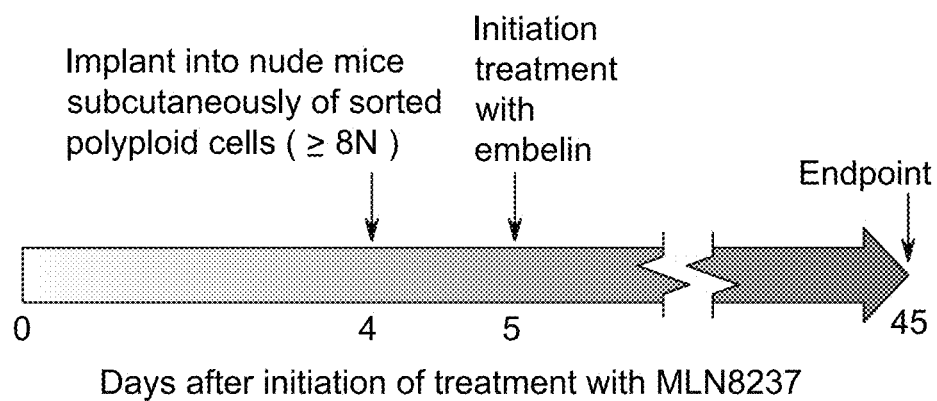
FIG. 7A is a graph which illustrates embelin suppressing tumorigenesis and metastasis of polyploid MM-BRAF cells induced by MLN8237.
Figure 7A:
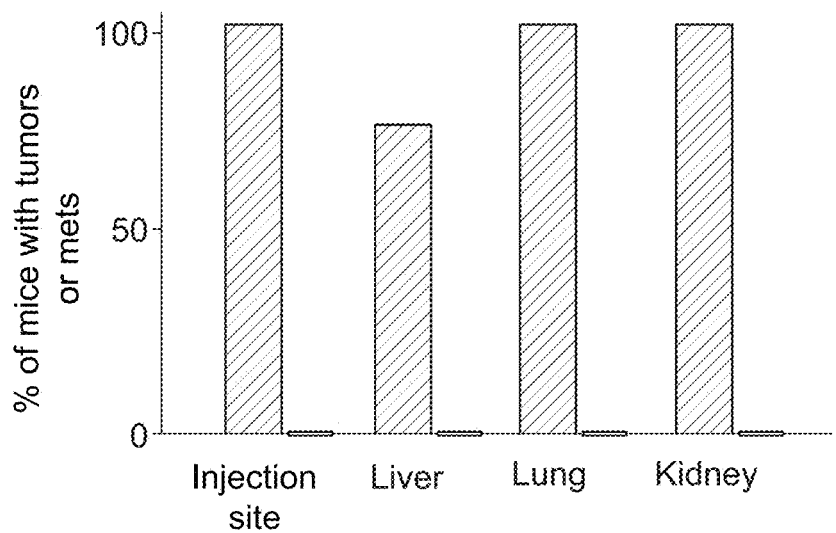
Figure 7B:
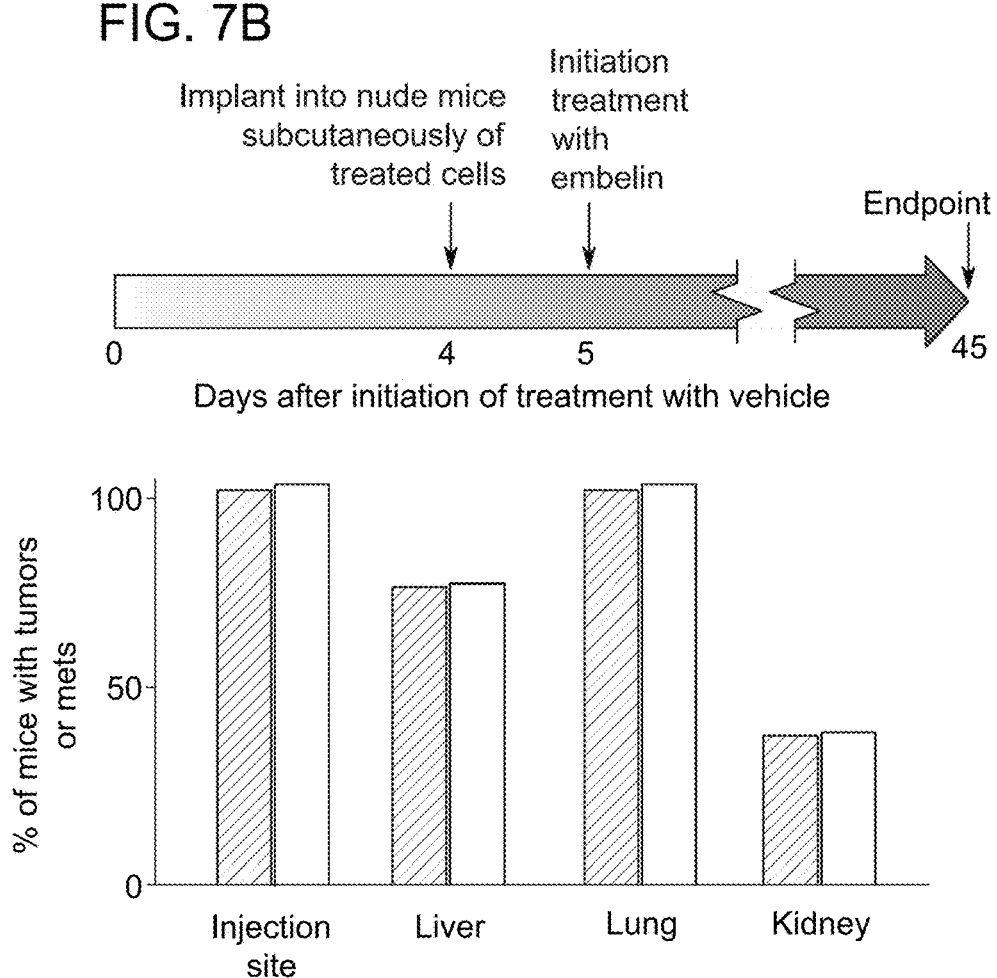
FIG. 7B is a graph which illustrates embelin failing to suppress tumorigenesis and metastasis of MM-BRAF cells.
Figure 7C:
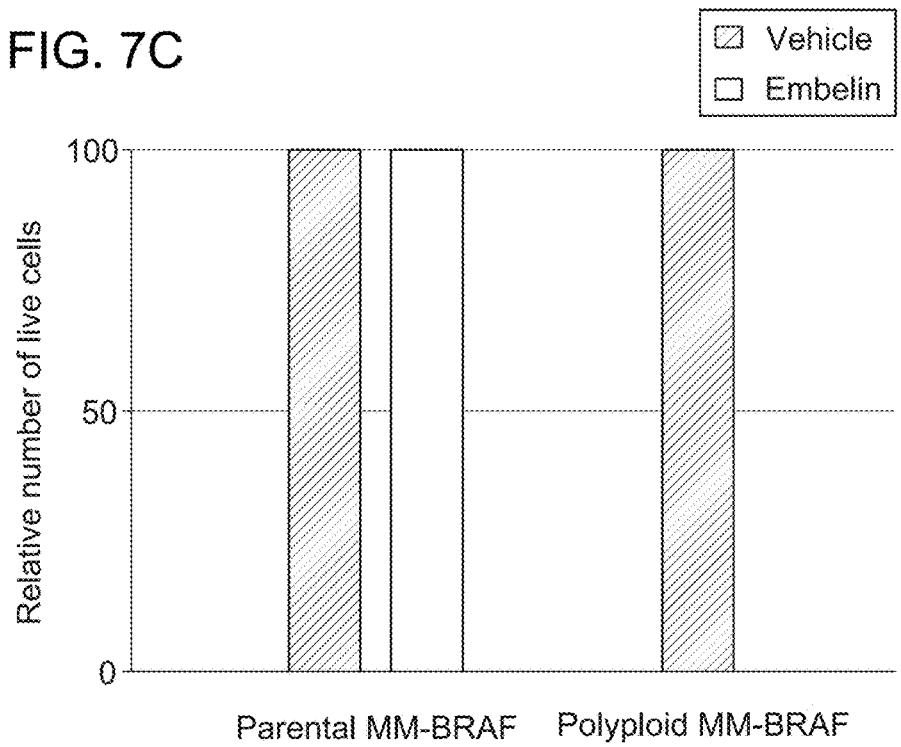
FIG. 7C is a graph which illustrates embelin selectively killing polyploid lung cancer cells as opposed to diploid cells.

Treatment with embelin (unfilled columns), however, completely blocked metastasis and drastically reduced tumor formation of polyploid MM-BRAF cells at the injection site (FIG. 7A). In contrast, tumorigenesis and metastasis of parental MMBRAF cells was only modestly affected (FIG. 7B). The contrast was mirrored by differential effect of embelin on polyploid and diploid MM-BRAF in vitro. Embelin selectively killed polyploid MM-BRAF cells but sparing their parental cells (FIG. 7C).

In another aspect, the present disclosure provides a pharmaceutical composition, which includes a compound of Formula I in admixture with a pharmaceutically acceptable excipient. One of skill in the art will recognize that the pharmaceutical compositions include the pharmaceutically acceptable salts of the compound of Formula I as described above.

In therapeutic and/or diagnostic applications, the compounds of the invention can be formulated for a variety of modes of administration, including systemic and topical or localized administration. Techniques and formulations generally may be found in Remington: The Science and Practice of Pharmacy (20$^{th}$ ed.) Lippincott, Williams & Wilkins (2000).

The compounds according to the invention are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A most preferable dosage is 10 to 30 mg per day. The exact dosage will depend upon the route of administration, the form in which the compound is administered, the subject to be treated, the body weight of the subject to be treated, and the preference and experience of the attending physician.

It was previously found that synthetic lethal interaction between MYC and disabling the chromosomal passenger protein complex elicits DNA endoreduplication and apoptosis. Polyploid cells survived apoptosis but eventually killed by a form of nonapoptotic cell death termed as autophagic cell death. Now, it has been found that expression of either Bcl-2 or Bcl-xL can rescue such polyploid cells from autophagic cell death. Thus, the expression of other antiapoptotic members of the Bcl2 family might serve the same purpose to confer resistance to MYC-VX680 synthetic lethality and subsequently allow generation of polyploid cells. This discovery allowed creation of a cell-based screening assay to identify small molecules that can selectively kill polyploid cells, as opposed to diploid cells. Using this assay, a library of natural product extracts was screened. Several extracts from the fruits of *Embelia ribes* Burm were discovered, and the bioactive ingredient from the extracts were further purified and finally identified the hydroxybenzoquinone embelin as the bioactive ingredient. With both purified and commercially available embelin, the therapeutic efficacy of the compound against multiple tumors such as breast cancer and lung cancer were demonstrated. The conclusion is that embelin may be useful to be combined with therapeutics that can induce polyploidy to prevent tumor relapse. Other derivatives of embelin might possess similar or even better bioavailability and therapeutic efficacy than embelin itself.

Examples

Materials and Methods
Cell Lines and Culture Media
Various RPEMYC derivatives used in this study were generated by stably transfecting human RPEMYC cells with a construct that expresses the gene of interest and selecting with 1 µg/ml of puromycin. Breast cancer cell line MD231MYC/Bcl2 was generated by engineering human MDA-MB-231 to stably express MYC and Bcl2. Lung cancer cell line MM-BRAF was created from mouse lung cancer model initiated by BRAF$^{V600E}$. All cell lines were cultured in DMEM supplemented with 10% fetal bovine serum and antibiotics at 5% CO$_2$ and 95% air in a humidified incubator.

Western Blot Analysis of Cell Extracts
Whole cell extracts were prepared by incubating cells for 15 min at 4° C. in a lysis buffer [50 mM Tris (pH 7.5), 200 mM NaCL, 0.1% SDS, 1% Triton X-100, 0.1 mM DTT, and 0.5 mM EGTA] supplemented with protease inhibitor mixture (BD Biosciences). The extracts were centrifuged at 8,000×g for 10 min to clear insoluble material. The protein concentration in the supernatant was determined using the Bio-Rad Protein Assay. Lysate containing 50-100 µg of proteins was resolved on NuPAGE (4-12%) Bis-Tris gels (Invitrogen) and transferred to nitrocellulose membranes (Bio-Rad). The membranes were blocked with 5% nonfat milk in PBS buffer for 1 h and then incubated overnight at 4° C. with primary antibodies diluted 1:1,000 in the blocking buffer. Rabbit polyclonal antibodies were used for Bcl-2, Bcl-xL and PCNA. Horseradish peroxidase conjugated anti-rabbit immunoglobulins were from Santa Cruz Biotechnology. Western blots were developed with the SuperSignal West Femto or Pico ECL detection kit (Thermo Scientific).

RNAi
XIAP esiRNAs were generated by digestion of double-stranded RNA corresponding to the full-length coding sequence of the cognate genes with *Escherichia coli* RNase III. The detailed protocol for preparation of esiRNA has been described elsewhere. esiRNAs smaller than 30 bp were purified with DEAE columns and were transfected into cells with Lipofectamine 2000 (Invitrogen) according to the manufacturer's instructions.

Small Molecules and Assays for Cell Death
Small molecules were purchased from commercial sources and used at the concentrations indicated in figure legends and figures. Cell death assays in response to drug treatment were performed 24 h after cells were seeded in 24-well plates. Each experiment was done in triplicate and each experiment was repeated at least twice unless indicated otherwise. Dead cells were identified by the trypan blue exclusion assay. All values are expressed as mean±1 SD of the mean.

Tumorigenicity Assays

Experimental mice were housed and treated according to the protocol approved by the Institutional Animal Care and Use Committee of MBICR. Assays for tumorigenicity were performed by injecting 3000 to 5 million cells in phosphate buffered saline (PBS) subcutaneously into the right flanks of BALB/c athymic mice. A cohort of five to ten mice was used for each group. In the treatment experiments, embelin 8 mg/kg was freshly dissolved in vehicle (10% DMSO, 100 mM Tris-HCl, pH 7.4) and administered by intraperitoneal injection every 48 h. The control group received injections of vehicle only. Tumor diameter at injection sites was monitored at the indicated time points with a digital caliper and the volume calculated using the formula: V (mm3)=A× B×B/2, where A and B represent the largest and smallest diameters of the tumor respectively. At the endpoint, mice were sacrificed to collect primary tumors and internal organs for analysis of metastasis.

Tumor Tissue Processing and Histology

Tumors were dissected away from mice and then either frozen in liquid nitrogen or fixed in 4% paraformaldehyde at room temperature overnight. Processing of tissues and staining of tissue sections with hematoxylin & eosin were performed by using standard methods.

Statistical Analysis

Statistical analyses were performed with the GraphPad Prism software. Statistical significance of the differences was evaluated with Student's unpaired two-tailed t test. P values less than 0.05 were considered statistically significant.

While the inventive features have been particularly shown and described with reference to preferred embodiments thereof, it will be understood by those in the art that the foregoing and other changes may be made therein without departing from the sprit and the scope of the disclosure. Likewise, the various diagrams may depict an example architectural or other configuration for the disclosure, which is done to aid in understanding the features and functionality that can be included in the disclosure. The disclosure is not restricted to the illustrated example architectures or configurations but can be implemented using a variety of alternative architectures and configurations. Additionally, although the disclosure is described above in terms of various exemplary embodiments and implementations, it should be understood that the various features and functionality described in one or more of the individual embodiments are not limited in their applicability to the particular embodiment with which they are described. They instead can be applied alone or in some combination, to one or more of the other embodiments of the disclosure, whether or not such embodiments are described, and whether or not such features are presented as being a part of a described embodiment. Thus, the breadth and scope of the present disclosure should not be limited by any of the above-described exemplary embodiments.

What is claimed is:

1. A method of identifying a compound that selectively kills polyploid cells, comprising:
converting a population of cells of a diploid cell line into a population of polyploid cells by incubating the diploid cell line with a polyploidy inducing agent or obtaining a population of polyploid cells that has been converted from a population of cells of a diploid cell line via incubation with a polyploidy inducing agent, wherein the diploid cell line overexpresses MYC and a Beclin 1 interacting protein compared to a non-diploid cell line;
screening one or more test compounds against the population of polyploid cells; and
identifying a compound, from the one or more test compounds, that selectively kills the population of polyploid cells to the same extent or to a greater extent as compared to embelin.

2. The method of claim 1, wherein the one or more test compounds has Formula I:

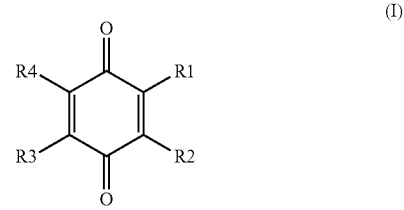

or a pharmaceutically acceptable salt thereof, wherein:
$R^1$ is independently selected from hydrogen, hydroxyl, amino, thiol, alkyl, alkenyl, alkynyl, cycloalkyl, cycloalkenyl, cycloalkynyl, alkylcycloalkyl, alkylcycloalkenyl, alkylcycloalkynyl, alkyloxy, alkyloxyalkyl, alkylamine, dialkylamine, arylamine, heterocyclyl, alkylheterocyclyl, aryl, alkylaryl, and heteroaryl, each optionally independently substituted with 1 to 6 substituents selected from hydrogen, halogen, nitro, amino, cyano, isocyano, thiol, hydroxyl, alkyl, cycloalkyl, alkoxy, aryloxy esteryl, and aryl;
$R^2$ is independently selected from alkyl, alkenyl, alkynyl, cycloalkyl, alkylcycloalkyl, alkoxy, and alkyloxyalkyl, each optionally independently substituted with 1 to 6 substituents selected from hydrogen, halogen, nitro, amino, cyano, isocyano, thiol, hydroxyl, alkyl, cycloalkyl, alkoxy, aryloxy, esteryl, and aryl;
$R^3$ and $R^4$ are each independently selected from hydrogen, hydroxyl, amino, thiol, alkyl, alkenyl, alkynyl, cycloalkyl, cycloalkenyl, cycloalkynyl, alkylcycloalkyl, alkylcycloalkenyl, alkylcycloalkynyl, alkyloxy, alkyloxyalkyl, alkylamine, dialkylamine, arylamine, heterocyclyl, heterocyclyl, alkylheterocyclyl, aryl, alkylaryl, and heteroaryl, each optionally independently substituted with 1 to 6 substituents selected from hydrogen, halogen, nitro, amino, cyano, isocyano, thiol, hydroxyl, alkyl, cycloalkyl, alkoxy, aryloxy esteryl, or aryl, or
$R^3$ and $R^4$ together form a 5 or 6-membered heteroaryl ring or a 6-membered aryl ring, each optionally independently substituted with 1 to 6 substituents selected from hydrogen, halogen, nitro, amino, cyano, isocyano, thiol, hydroxyl, alkyl, cycloalkyl, alkoxy, aryloxy esteryl, or aryl.

3. The method of claim 2, wherein:
$R^1$ is independently selected from hydrogen, hydroxyl, amino, thiol, $(C_1\text{-}C_{20})$alkyl, $(C_2\text{-}C_{20})$alkenyl, $(C_2\text{-}C_{20})$alkynyl, $(C_3\text{-}C_{20})$cycloalkyl, $(C_5\text{-}C_{20})$cycloalkenyl, $(C_8\text{-}C_{20})$cycloalkynyl, $(C_1\text{-}C_{20})$alkyl$(C_3\text{-}C_{20})$cycloalkyl, $(C_1-C_{20})$alkyl$(C_5-C_{20})$cyclo-alkenyl, $(C_1-C_{20})$alkyl$(C_8-C_{20})$cycloalkynyl, $(C_1-C_{20})$alkyloxy, $(C_1-C_{20})$alkyloxy$(C_1-C_{20})$alkyl, $(C_1-C_{20})$alkylamine, $(C_1-C_{20})$dialkylamine, arylamine, heterocyclyl, $(C_1-C_{20})$alkylheterocyclyl, aryl, $(C_1-C_{20})$alkylaryl, and heteroaryl, each optionally independently substituted with 1 to 6 substituents selected from hydrogen, halogen, nitro, amino, cyano, isocyano, thiol, hydroxyl, $(C_1-C_6)$alkyl, $(C_3-C_{20})$cycloalkyl, $(C_1-C_{20})$alkoxy, aryloxy, esteryl, and aryl;

$R^2$ is independently selected from $(C_1-C_{20})$alkyl, $(C_2-C_{20})$alkenyl, $(C_2-C_{20})$alkynyl, $(C_3-C_{20})$cycloalkyl, $(C_1-C_{20})$alkyl$(C_3-C_{20})$cycloalkyl, $(C_1-C_{20})$alkoxy, and $(C_1-C_{20})$alkyloxy$(C_1-C_{20})$alkyl, each optionally independently substituted with 1 to 6 substituents selected from hydrogen, halogen, nitro, amino, cyano, isocyano, thiol, hydroxyl, $(C_1-C_{20})$alkyl, $(C_3-C_{20})$cycloalkyl, $(C_1-C_{20})$alkoxy, aryloxy, esteryl, and aryl;

$R^3$ and $R^4$ are each independently selected from hydrogen, hydroxyl, amino, thiol, $(C_1-C_{20})$alkyl, $(C_2-C_{20})$alkenyl, $(C_2-C_{20})$alkynyl, $(C_3-C_{20})$cycloalkyl, $(C_5-C_{20})$cycloalkenyl, $(C_8-C_{20})$cycloalkynyl, $(C_1-C_{20})$alkyl$(C_3-C_{20})$cycloalkyl, $(C_1-C_{20})$alkyl$(C_5-C_{20})$cycloalkenyl, $(C_1-C_{20})$alkyl$(C_8-C_{20})$cycloalkynyl, $(C_1-C_{20})$alkyloxy, $(C_1-C_{20})$alkyloxy$(C_1-C_{20})$alkyl, $(C_1-C_{20})$alkylamine, $(C_1-C_{20})$dialkylamine, arylamine, heterocyclyl, alkylheterocyclyl, aryl, alkylaryl, and heteroaryl, each optionally independently substituted with 1 to 6 substituents selected from hydrogen, halogen, nitro, amino, cyano, isocyano, thiol, hydroxyl, $(C_1-C_{20})$alkyl, $(C_3-C_{20})$cycloalkyl, $(C_1-C_{20})$alkoxy, aryloxy, esteryl, and aryl, or $R^3$ and $R^4$ together form a 5 or 6 membered heterocyclic or heteroaryl ring or a 6 membered aryl ring, each optionally independently substituted with 1 to 6 substituents selected from hydrogen, halogen, nitro, amino, cyano, isocyano, thiol, hydroxyl, $(C_1-C_{20})$alkyl, $(C_3-C_{20})$cycloalkyl, $(C_1-C_{20})$alkoxy, aryloxy, esteryl, and aryl.

4. The method of claim 2, wherein:

$R^3$ and $R^4$ together form a 5-membered heterocyclic ring selected from substituted or unsubstituted pyrrolidine, substituted or unsubstituted pyrazolidine, substituted or unsubstituted imidazolidine, substituted or unsubstituted tetrahydrofuran, and substituted or unsubstituted tetrahydrothiophene, or $R^3$ and $R^4$ together form a 5-membered heteroaryl ring selected from substituted or unsubstituted furan, substituted or unsubstituted thiophene, substituted or unsubstituted oxazole, substituted or unsubstituted isoxazole, substituted or unsubstituted indole, substituted or unsubstituted benzofuran, and substituted or unsubstituted benzo[b]thiophene, or $R^3$ and $R^4$ together form a 6-membered heterocyclic ring selected from substituted or unsubstituted piperidine, substituted or unsubstituted piperazine, substituted or unsubstituted thiane, substituted or unsubstituted morpholine, and substituted or unsubstituted thiomorpholine, or $R^3$ and $R^4$ together form a 6-membered heteroaryl ring selected from substituted or unsubstituted pyridine, substituted or unsubstituted pyridazine, substituted or unsubstituted pyrimidine, substituted or unsubstituted pyrazine, and substituted or unsubstituted morpholine, or $R^3$ and $R^4$ together form a 6-membered aryl ring selected from substituted or unsubstituted phenyl, substituted or unsubstituted biphenyl, and substituted or unsubstituted naphthyl.

5. The method of claim 2, wherein:

$R^1$ is independently selected from hydroxyl;
$R^2$ is independently selected from $(C_1-C_{20})$alkyl;
$R^3$ is independently selected from hydroxyl; and
$R^4$ is independently selected from hydrogen.

6. The method of claim 1, wherein the Beclin 1 interacting protein is a Bcl-2 family member.

7. The method of claim 6, wherein the Bcl-2 family member is Bcl-2 or Bcl-$X_L$.

8. The method of claim 1, wherein the polyploidy inducing agent is an Aurora Kinase inhibitor.

9. The method of claim 8, wherein the Aurora kinase inhibitor is an Aurora Kinase B inhibitor.

10. The method of claim 9, wherein the Aurora kinase inhibitor is VX680 or AZD1152.

11. The method of claim 8, wherein the Aurora kinase inhibitor is an Aurora Kinase A inhibitor.

12. The method of claim 1, wherein the population of polyploid cells is a homogeneous population of polyploid cells.

13. The method of claim 1, wherein the expression of the Beclin 1 interacting protein protects the population of polyploid cells from apoptotic or autophagic cell death caused by incubating the diploid cell line with at least one polyploidy inducing agent.

14. A method of identifying a compound that selectively kills polyploid cells, comprising:

incubating a population of cells of a diploid cell line overexpressing MYC and a Beclin 1 interacting protein with an polyploidy inducing agent to convert the diploid cell line into a population of polyploid cells or obtaining a population of polyploid cells that has been converted from a population of cells of a diploid cell line via incubation with a polyploidy inducing agent, wherein the diploid cell line overexpresses MYC and Beclin 1 interacting protein compared to a non-diploid cell line;

screening one or more test compounds against the population of polyploid cells and the population of cells of the diploid cell line; and identifying, from the one or more test compounds, a compound that selectively kills the population of polyploid cells as compared to the diploid cell line.

15. The method of claim 14, wherein the polyploidy inducing agent is an Aurora Kinase inhibitor.

16. The method of claim 14, wherein the Beclin 1 interacting protein is a Bcl2 family member.

17. A method of identifying a compound that selectively kills polyploid cells, comprising:

incubating a population of cells of a diploid cell line overexpressing MYC and a Beclin 1 interacting protein with polyploidy inducing agent to convert the diploid cell line into a population of polyploid cells; wherein the MYC and Beclin 1 interacting protein are overexpressed compared to a non-diploid cell line;

the Beclin 1 interacting protein is a Bcl2 family member; and wherein the polyploidy inducing agent is an Aurora Kinase inhibitor;

screening one or more test compounds against the population of polyploid cells; and identifying, from the one or more test compounds, a compound that selectively kills the population of polyploid cells to the same extent or a greater extent as compared to embelin; and wherein
the one or more test compounds has Formula I:

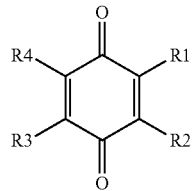
(I)

or a pharmaceutically acceptable salt thereof, wherein:
$R^1$ is independently selected from hydrogen, hydroxyl, amino, thiol, alkyl, alkenyl, alkynyl, cycloalkyl, cycloalkenyl, cycloalkynyl, alkylcycloalkyl, alkylcycloalkenyl, alkylcycloalkynyl, alkyloxy, alkyloxyalkyl, alkylamine, dialkylamine, arylamine, heterocyclyl, alkylheterocyclyl, aryl, alkylaryl, and heteroaryl, each optionally independently substituted with 1 to 6 substituents selected from hydrogen, halogen, nitro, amino, cyano, isocyano, thiol, hydroxyl, alkyl, cycloalkyl, alkoxy, aryloxy esteryl, and aryl;
$R^2$ is independently selected from alkyl, alkenyl, alkynyl, cycloalkyl, alkylcycloalkyl, alkoxy, and alkyloxyalkyl, each optionally independently substituted with 1 to 6 substituents selected from hydrogen, halogen, nitro, amino, cyano, isocyano, thiol, hydroxyl, alkyl, cycloalkyl, alkoxy, aryloxy, esteryl, and aryl;
$R^3$ and $R^4$ are each independently selected from hydrogen, hydroxyl, amino, thiol, alkyl, alkenyl, alkynyl, cycloalkyl, cycloalkenyl, cycloalkynyl, alkylcycloalkyl, alkylcycloalkenyl, alkylcycloalkynyl, alkyloxy, alkyloxyalkyl, alkylamine, dialkylamine, arylamine, heterocyclyl, heterocyclyl, alkylheterocyclyl, aryl, alkylaryl, and heteroaryl, each optionally independently substituted with 1 to 6 substituents selected from hydrogen, halogen, nitro, amino, cyano, isocyano, thiol, hydroxyl, alkyl, cycloalkyl, alkoxy, aryloxy esteryl, or aryl, or
$R^3$ and $R^4$ together form a 5 or 6-membered heteroaryl ring or a 6-membered aryl ring, each optionally independently substituted with 1 to 6 substituents selected from hydrogen, halogen, nitro, amino, cyano, isocyano, thiol, hydroxyl, alkyl, cycloalkyl, alkoxy, aryloxy esteryl, or aryl.

18. The method of claim 17, wherein
$R^3$ and $R^4$ together form a 5-membered heterocyclic ring selected from substituted or unsubstituted pyrrolidine, substituted or unsubstituted pyrazolidine, substituted or unsubstituted imidazolidine, substituted or unsubstituted tetrahydrofuran, and substituted or unsubstituted tetrahydrothiophene, or
$R^3$ and $R^4$ together form a 5-membered heteroaryl ring selected from substituted or unsubstituted furan, substituted or unsubstituted thiophene, substituted or unsubstituted oxazole, substituted or unsubstituted isoxazole, substituted or unsubstituted indole, substituted or unsubstituted benzofuran, and substituted or unsubstituted benzo[b]thiophene, or
$R^3$ and $R^4$ together form a 6-membered heterocyclic ring selected from substituted or unsubstituted piperidine, substituted or unsubstituted piperazine, substituted or unsubstituted thiane, substituted or unsubstituted morpholine, and substituted or unsubstituted thiomorpholine, or
$R^3$ and $R^4$ together form a 6-membered heteroaryl ring selected from substituted or unsubstituted pyridine, substituted or unsubstituted pyridazine, substituted or unsubstituted pyrimidine, substituted or unsubstituted pyrazine, and substituted or unsubstituted morpholine, or
$R^3$ and $R^4$ together form a 6-membered aryl ring selected from substituted or unsubstituted phenyl, substituted or unsubstituted biphenyl, and substituted or unsubstituted naphthyl.

19. The method of claim 17, wherein:
$R^1$ is independently selected from hydroxyl;
$R^2$ is independently selected from $(C_1-C_{20})$alkyl;
$R^3$ is independently selected from hydroxyl; and
$R^4$ is independently selected from hydrogen.

* * * * *